US006232525B1

(12) United States Patent
Ryals et al.

(10) Patent No.: US 6,232,525 B1
(45) Date of Patent: May 15, 2001

(54) MUTANT PLANTS AND USES THEREFOR

(75) Inventors: John Andrew Ryals, Cary; Scott Joseph Uknes, Apex; Eric Russell Ward, Durham, all of NC (US); Terrence Patrick Delaney, Ithaca, NY (US)

(73) Assignee: Novartis Finance Corporation, New York, NY (US)

( * ) Notice: Subject to any disclaimer, the term of this patent is extended or adjusted under 35 U.S.C. 154(b) by 0 days.

(21) Appl. No.: 09/223,535

(22) Filed: Dec. 30, 1998

Related U.S. Application Data

(60) Division of application No. 08/992,801, filed on Dec. 18, 1997, now Pat. No. 6,107,544, which is a continuation-in-part of application No. 08/648,949, filed on May 16, 1996, now Pat. No. 5,792,904, which is a continuation-in-part of application No. 08/165,238, filed on Dec. 10, 1993, now abandoned, which is a continuation-in-part of application No. 08/002,285, filed on Jan. 8, 1993, now abandoned.

(51) Int. Cl.$^7$ .............................. A01H 1/00; A01H 1/04

(52) U.S. Cl. .................... 800/265; 800/260; 800/301; 435/5

(58) Field of Search .................................. 800/265, 260, 800/270, 278, 279, 301; 47/58.1; 435/4, 5, 69.1, 172.1

(56) References Cited

U.S. PATENT DOCUMENTS 5,614,395  3/1997  Ryals et al. .
5,792,904  8/1998  Ryals et al. .

FOREIGN PATENT DOCUMENTS 0306139   3/1989   (EP) .
0317239   5/1989   (EP) .
0320130   6/1989   (EP) .
0392225   10/1990  (EP) .
0440304   8/1991   (EP) .
WO89/07647 8/1989  (WO) .
WO94/16077 7/1994  (WO) .
WO95/19443 7/1995  (WO) .

OTHER PUBLICATIONS

Century et al. Proc. Natl. Acad. Sci., vol. 92, pp. 6597–6601.*
Gaffney etal. Science vol. 261, pp. 754–756, 1993.*
Alexander, D., et al., "Systemic Acquired Resistance in Tobacco: Use of Transgenic Expression to Study the Functions of Pathogenesis–Related Proteins", *Current Plant Science and Biotechnology in Agriculture*, (Advances in Molecular Genetics of Plant–Microbe Interactions vol. 2.) 6th International Symposium on Washington, 14: 527–533 (1992).

Alexander, D., et al., "Increased Tolerance to Two Oomycete Pathogens in Transgenic Tobacco Expressing Pathogenesis–related Protein 1a", *PNAS*, 90: 7327–7331 (1993).
Bol, J.F., et al., "Plant Pathogenesis–related Proteins Induced by Virus Infection", *Annu. Rev. Phytopathol.*, 28: 113–138 (1990).
Bowling et al., "A Mutation in Arabidopsis That Leads to Constitutive Expression of Systemic Acquired Resistance", *The Plant Cell*, 6: 1845–1857 (1994).
Bowling et al., "The cpr5 Mutant of Arabidopsis Expressed Both NPR1–Dependent and NPR1–Independent Resistance", *The Plant Cell*, 9: 1573–1584 (1997).
Cameron et al., "Biologically induced systemic acquired resistance in *Arabidopsis thaliana*", *The Plant Journal* 5(5): 715–725 (1994).
Cao et al., "Characterization of an Arabidopsis Mutant That Is Nonresponsive to Inducers of Systemic Acquired Resistance", *The Plant Cell*, 6: 1583–1592 (1994).
Cao et al., "The Arabidopsis NPR1 Gene that Controls Systemic Acquired Resistance Encodes a Novel Protein Containing Ankyrin Repeats", *Cell*, 88: 57–63 (1997).
Century et al., "NDR1, a locus of *Arabidopsis thaliana* that is required for disease resistance to both a bacterial and a fungal protein", *Proc. Natl. Acad. Sci.*, 92: 6597–6601 (1995).
Crop Science Society of America, In Glossary of Crop Science Terms. p. 18 (1992).
Dangl, J.L., "Applications of *Arabidopsis thaliana* to Outstanding Issued in Plant–Pathogen Interactions", *International Review of Cytology*, 144: 53–83 (1993).
Dangl et al., "Death Don't Have No Mercy: Cell Death Programs in Plant–Microbe Interactions", *The Plant Cell*, 8: 1793–1807 (1996).
Debener, T., et al;., "Identification and Molecular Mapping of a Single *Arabidopsis thaliana* Locus Determining Resistance to a Phytopathogenic *Pseudomonas syringae* Isolate", *The Plant Journal*, 1(3): 289–302 (1991).

(List continued on next page.)

*Primary Examiner*—Paula Hutzell
*Assistant Examiner*—Melissa L. Kimball
(74) *Attorney, Agent, or Firm*—J. Timothy Meigs

(57) ABSTRACT

Methods are provided for selecting parental plants exhibiting disease resistance and for using these plants in breeding programs. In one method of the invention, constitutive immunity (cim) mutants are screened for either resistance to a pathogen of interest or for the expression of systemic acquired resistance (SAR) genes. Such mutants having the desired traits or expressing the desired genes are then used in breeding programs. Parent plants can also be selected based on the constitutive expression of SAR genes. These mutants are phenotypically normal yet exhibit a significant level of disease resistance. Also disclosed are lesion-simulating-disease (lsd) mutants having a lesion mimic phenotype that also express SAR genes and exhibit disease resistance. Further disclosed are non-inducible immunity (nim) mutants that do not express SAR genes, even when induced by a pathogen. Methods of use for these mutants are also disclosed.

12 Claims, No Drawings

OTHER PUBLICATIONS

Delaney, T.P., et al., "A Central Role of Salicylic Acid in Plant Disease Resistance", Science, 266: 1247–1250 (1994).

Delaney et al., "Arabidopsis signal transduction mutants defective in chemically and biologically induced disease resistance", Abstract, 6$^{th}$ International Meeting on Arabidopsis Research, (1995).

Delaney et al., "Arabidopsis signal transduction mutant defective in chemically and biologically induced disease resistance", Proc. Natl. Acad. Sci., 92: 6602–6606 (1995).

Delaney, T.P., "Genetic Dissection of Acquired Resistance to Disease", Plant Physiol. 113: 5–12 (1997).

Dietrich, R.A., et al., "Arabidopsis Mutants Simulating Disease Resistance Response", Cell, 77: 565–577 (1994).

Evans et al., "Disease Resistance: Incorporation into Sexually Incompatible Somatic Hybrids of the Genus Nicotiana", Science, 213: 907–909 (1981).

Gaffney, T., et al., "Requirement of Salicylic Acid for the Induction of Systemic Acquired Resistance", Science, 261: 754–756 (1993).

Glascock, C.B., et al., "Transgenic Tobacco Resistant to Phytophthora Parasitica: Analysis of Expression and Activity of a Novel Pathogenesis–related (PR) Protein, SAR 8.2", Abstract Y205, J. Cell. Biochem. Suppl., (Keystone Symposium on Crop Improvement Via Biotechnology, Apr. 10–16, 1992) 16F: 215 (1992).

Glazebrook et al., "Isolation of Arabidopsis Mutants With Enhanced Disease Susceptibility by Direct Screening", Genetics 143: 973–982 (1996).

Greenberg et al., "Programmed Cell Death in Plants: A Pathogen–Triggered Response Activated Coordinately with Multiple Defense Functions", Cell 77: 551–563 (1994).

Helentjaris, T., et al., "Construction of Genetic Linkage Maps in maize and Tomato Using Restriction Fragment Length Polymorphisma", Theor. Appl. Genet., 72: 761–769 (1986).

Huang, H. et al., "An Improved Procedure for Transforming Arabidopsis thaliana (Landsberg erecta)Root Explant", Plant Molecular Biology Reporter, 10(4): 372–383 (1992).

Hunt et al., "Systemic Acquired Resistance Signal Transduction", Critical Reviews in Plant Sciences 15: 583–606 (1996).

Kuc, Joseph, "Induced Immunity to Plant Disease", BioScience, 32(11): 854–860 (1982).

Langford, A.N., "Autogenous Necrosis in Tomatoes Immune from Cladosporium fulvum Cooke", Canadian Journal of Research, 26(C): 35–64 (1947).

Lawton, K., et al., "The Molecular Biology of Systemic Acquired Resistance", Proceedings of the 2nd European Federation of Plant Pathology Conference, pp. 1–13 (1992).

Lawton, K., et al., "The Molecular Biology of Systemic Acquired Resistance", Developments in Plant Pathology (Mechanisms of Plant Defense Responses), 2nd Int'l Conference of the European Foundation for Plant Pathology, Strasbourg, France, Aug. 24–27, 1992, 2: 422–432 (1993).

Linthorst, H.J.M., et al., "Analysis of Acidic and Basic Chitinases From Tobacco and Petunia and Their Constitutive Expression in Transgneic Tobacco", Molecular Plant–Microbe Interactions, 3(4): 252–258 (1990).

Mauch–Mani et al., "Systemic Acquired Resistance in Arabidopsis thaliana Induced by a Predisposing Infection with a Pathogenic Isolate of Fusarium oxysporum", Molecular Plant–Microbe Interactions 7: 378–383 (1994).

Michelmore, R.W., et al., "Identification of Markers Linked to Disease–resistance Genes by Bulked Segregant Analysis: A Rapid Method to Detect Markers in Specific Genomic Regions by Using Segregating Populations", Proc. Natl. Acad. Sci., 88: 9828–9832 (1991).

Mindrinos et al., "The A. thaliana Disease Resistance Gene RPS2 Encodes a Protein Containing a Nucleotide–Binding Site and Leucine–Rich Repeats", Cell 78: 1089–1099 (1994).

Moffat, A.S., "Gene Research Flowers in Arabidopsis thaliana", Science, 258: 1580–1581 (1992).

Neuffer, M.G., et al., "Dominant Disease Lesion Mimics in Maize", The Journal of Heridity, 66: 265–270 (1975).

Neuffer, M.G., et al., "Gene Structure and Function in Higher Plants", Proceedings of the Int'l Symposium held at Hyderabad, India, Dec. 7–9, 1983, G.M. Reedy and E.H. Coe, Jr., (Eds) Oxxford & IBH Publishing Co., 124–134 (1983).

Parker et al., "Characterization of eds1, a Mutation in Arabidopsis Suppressing Resistance to Peronospora parasitica Specified by Several Different RPP Genes", The Plant Cell 8: 2033–2046 (1996).

Reuveni R., et al., Abstract #A1104, "Systemic Resistance Against Northern Leaf Blight and Common Rust in Maize Induced by Foliar Spray of Phosphates", Phytopath, 82(10): 1179 (1992).

Ross, A.F., "Localized Acquired Resistance to Plant Virus Infection in Hypersensitive Hosts", Virology, 14: 329–339 (1961).

Ross, A.F., "Systemic Acquired Resistance Induced by Localized Virus Infections in Plants", Virology, 14: 340–358 (1961).

Ross, A.F., "Systemic Effects of Local Lesion Formation", in Viruses of Plants, A.B.R. Beemster and J. Dijkstra, eds (Amsterdam: North–Holland), pp. 127–150 (1966).

Ryals J., et al., "The Molecular Biology of Systemic Acquired Resistance", Abstract Y008, J. Cell. Biochem. Suppl., (Keystone Symposium on Crop Improvement Via Biotechnology, Apr. 10–16, 1992), 16F: 200 (1992).

Ryals et al., "Signal transduction in systemic acquired resistance", Proc. Natl. Acad. Sci. USA 92: 4202–4205 (1995).

Ryals et al., "Systemic Acquired Resistance", The Plant Cell 8: 1809–1819 (1996).

Ryals et al., "The Arabidopsis NIM1 Protein Shows Homology to the Mammalian Transcription Factor Inhibitor IkB", The Plant Cell 9: 425–439 (1997).

Simmonds, In Principles of Crop Improvement, pp. 274–276 (1979).

Uknes, S., et al., "Acquired Resistance in Arabidopsis", The Plant Cell, 4: 645–656 (1992).

Uknes, S., et al., "Biological Induction of Systemic Acquired Resistance in Arabidopsis", *MPMI,* 6(6): 692–698 (1993).

Uknes et al., "Reduction of risk for growers: methods for the development of disease–resistant crops", *New Phytol.* 133: 3–10 (1996).

Walbot, V., et al., "Disease Lesion Mimic Mutations", *Genetic Engineering of Plants,* Tsuno Kosug, Carole P. Meredith and Alexander Hollaender (eds), Plenum Publishing Corp., pp. 431–442 (1983).

Ward, E.R., e tal., "Coordinate Gene Activity in Response to Agents that Induce Systemic Acquired Resistance", *The Plant Cell,* 3: 1085–1094 (1991).

Weyman, K., et al., "Suppression and Restoration of Lesion Formation in Arabidopsis lsd Mutants", *The Plant Cell,* 7: 2013–2022 (1995).

* cited by examiner

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
       (A) LENGTH: 14113 base pairs
       (B) TYPE: nucleic acid
       (C) STRANDEDNESS: single
       (D) TOPOLOGY: linear (ii) MOLECULE TYPE: other nucleic acid
       (A) DESCRIPTION: /desc = "PR-1/luc construct"

(xi) SEQUENCE DESCRIPTION: SEQ ID NO: 1:

```
GCGGTATCGG TGCAGATTAT TTGGATTGAG AGTGAATATG AGACTCTAAT TGGATACCGA        60

GGGGAATTTA TGGAACGTCA GTGGAGCATT TTTGACAAGA AATATTTGCT AGCTGATAGT       120

GACCTTAGGC GACTTTTGAA CGCGCAATAA TGGTTTCTGA CGTATGTGCT TAGCTCATTA       180

AACTCCAGAA ACCCGCGGCT GAGTGGCTCC TTCAACGTTG CGGTTCTGTC AGTTCCAAAC       240

GTAAAACGGC TTGTCCCGCG TCATCGGCGG GGGTCATAAC GTGACTCCCT TAATTCTCCG       300

CTCATGATCA GATTGTCGTT TCCCGCCTTC AGTTTAAACT ATCAGTGTTT GACAGGATAT       360

ATTGGCGGGT AAACCTAAGA GAAAAGAGCG TTTATTAGAA TAATCGGATA TTTAAAAGGG       420

CGTGAAAAGG TTTATCCGTT CGTCCATTTG TATGTGCATG CCAACCACAG GGTTCCCCTC       480

GGGAGTGCTT GGCATTCCGT GCGATAATGA CTTCTGTTCA ACCACCCAAA CGTCGGAAAG       540

CCTGACGACG GAGCAGCATT CCAAAAAGAT CCCTTGGCTC GTCTGGGTCG GCTAGAAGGT       600

CGAGTGGGCT GCTGTGGCTT GATCCCTCAA CGCGGTCGCG GACGTAGCGC AGCGCCGAAA       660

AATCCTCGAT CGCAAATCCG ACGCTGTCGA AAAGCGTGAT CTGCTTGTCG CTCTTTCGGC       720

CGACGTCCTG GCCAGTCATC ACGCGCCAAA GTTCCGTCAC AGGATGATCT GGCGCGAGTT       780

GCTGGATCTC GCCTTCAATC CGGGTCTGTG GCGGGAACTC CACGAAAATA TCCGAACGCA       840

GCAAGATCCC TTTCCGACGC TCACCGGGCT GGTTGCCCTC GCCGCTGGGC TGGCGGCCGT       900

CTATGGCCCT GCAAACGCGC CAGAAACGCC GTCGAAGCCG TGTGCGAGAC ACCGCGGCCG       960

CCGGCGTTGT GGATACCTCG CGGAAAACTT GGCCCTCACT GACAGATGAG GGGCGGACGT      1020

TGACACTTGA GGGGCCGACT CACCCGGCGC GGCGTTGACA GATGAGGGGC AGGCTCGATT      1080

TCGGCCGGCG ACGTGGAGCT GGCCAGCCTC GCAAATCGGC GAAAACGCCT GATTTTACGC      1140

GAGTTTCCCA CAGATGATGT GGACAAGCCT GGGGATAAGT GCCCTGCGGT ATTGACACTT      1200

GAGGGGCGCG ACTACTGACA GATGAGGGGC GCGATCCTTG ACACTTGAGG GGCAGAGTGC      1260

TGACAGATGA GGGGCGCACC TATTGACATT TGAGGGGCTG TCCACAGGCA GAAAATCCAG      1320

CATTTGCAAG GGTTTCCGCC CGTTTTTCGG CCACCGCTAA CCTGTCTTTT AACCTGCTTT      1380

TAAACCAATA TTTATAAACC TTGTTTTTAA CCAGGGCTGC GCCCTGTGCG CGTGACCGCG      1440

CACGCCGAAG GGGGGTGCCC CCCCTTCTCG AACCCTCCCG GCCCGCTAAC GCGGGCCTCC      1500

CATCCCCCCA GGGGCTGCGC CCCTCGGCCG CGAACGGCCT CACCCCAAAA ATGGCAGCCA      1560

AGCTTCGGGC TGAAATTGCA GGACAACTGG TGAGTCTGGA TCTGAAGTTG AATAGTGTCA      1620

TGGATGATCT GGACCGACTG GAGCCATCCC CAAGGTGGCG GAAGAGTTCC AGCGTGGTGG      1680

GTAGCAGTAG CCCGATATGC CCCGGTTGAC CCAAAGTGTC TGTTATGACA GGCAGATTAT      1740
```

```
CAACTCATGC CGTTGAACAT AGGCTGAATA TCGAAGATGG CAGCCGTTAT CTCCAGAAAA   1800

TCATTCAGCT TAGTTTTAAA TTACCCCGAC CTGAAGCCTT TGATTTACGT AATGAATTTC   1860

GCCAGCGGGC TGAGGCTCTA TATCAGCAAA TTAATAATCA ACCGCCAGAC TCTGGAATGG   1920

TAAGGGATCT CATCGCGGTG ACTGATACCT ATGGTGCCGC ACTTTCGACG CCACGGGAAA   1980

TCCATCAGGC CATTAATTCC CTGATTTTTC TTTATCCGGG GATGCGGGAT TTTGTTTATT   2040

TCCCTGATTT GTGCCTGCTT CAGCTTATAC GGGTGACAAA CCCGGCTCTG TATGACTGGA   2100

CAGAGCATTA CCTGACAGAA CGGTCCGTGA TTGAAACCGG TCAGGGTATG CTTTCTGACG   2160

GAGAGAAAGC AGACTTCCGG GAGGGGCTTA TCAGATGTAT GAAGACGTTC AGGGCATCAA   2220

ATGCAGACTC GTTTCTGACA CTTGCAGACT GGATCTATCT CATCTGCGCA AGGCAGAACG   2280

TGAAGACGGC CGCCCTGGAC CTCGCCCGCG AGCGCCAGGC GCACGAGGCC GGCGCGCGGA   2340

CCCGCGCCAC GGCCCACGAG CGGACGCCGC AGCAGGAGCG CCAGAAGGCC GCCAGAGAGG   2400

CCGAGCGCGG CCGTGAGGCT TGGACGCTAG GGCAGGGCAT GAAAAAGCCC GTAGCGGGCT   2460

GCTACGGGCG TCTGACGCGG TGGAAAGGGG GAGGGGATGT TGTCTACATG GCTCTGCTGT   2520

AGTGAGTGGG TTGCGCTCCG GCAGCGGTCC TGATCAATCG TCACCCTTTC TCGGTCCTTC   2580

AACGTTCCTG ACAACGAGCC TCCTTTTCGC CAATCCATCG ACAATCACCG CGAGTCCCTG   2640

CTCGAACGCT GCGTCCGGAC CGGCTTCGTC GAAGGCGTCT ATCGCGGCCC GCAACAGCGG   2700

CGAGAGCGGA GCCTGTTCAA CGGTGCCGCC GCGCTCGCCG GCATCGCTGT CGCCGGCCTG   2760

CTCCTCAAGC ACGGCCCCAA CAGTGAAGTA GCTGATTGTC ATCAGCGCAT TGACGGCGTC   2820

CCCGGCCGAA AAACCCGCCT CGCAGAGGAA GCGAAGCTGC GCGTCGGCCG TTTCCATCTG   2880

CGGTGCGCCC GGTCGCGTGC CGGCATGGAT GCGCGCGCCA TCGCGGTAGG CGAGCAGCGC   2940

CTGCCTGAAG CTGCGGGCAT TCCCGATCAG AAATGAGCGC CAGTCGTCGT CGGCTGTCGG   3000

CACCGAATGC GTATGATTCT CCGCCAGCAT GGCTTCGGCC AGTGCGTCGA GCAGCGCCCG   3060

CTTGTTCCTG AAGTGCCAGT AAAGCGCCGG CTGCTGAACC CCCAACCGTT CCGCCAGTTT   3120

GCGTGTCGTC AGACCGTCTA CGCCGACCTC GTTCAACAGG TCCAGGGCGG CACGGATCAC   3180

TGTATTCGGC TGCAACTTTG TCATGCTTGA CACTTTATCA CTGATAAACA TAATATGTCC   3240

ACCAACTTAT CAGTGATAAA GAATCCGCGC GTTCAATCGG ACCAGCGGAG GCTGGTCCGG   3300

AGGCCAGACG TGAAACCCAA CATACCCCTG ATCGTAATTC TGAGCACTGT CGCGCTCGAC   3360

GCTGTCGGCA TCGGCCTGAT TATGCCGGTG CTGCCGGGCC TCCTGCGCGA TCTGGTTCAC   3420

TCGAACGACG TCACCGCCCA CTATGGCATT CTGCTGGCGC TGTATGCGTT GGTGCAATTT   3480

GCCTGCGCAC CTGTGCTGGG CGCGCTGTCG GATCGTTTCG GGCGGCGGCC AATCTTGCTC   3540

GTCTCGCTGG CCGGCGACCT GCAGGGGGGG GGGGAAAGC CACGTTGTGT CTCAAAATCT   3600

CTGATGTTAC ATTGCACAAG ATAAAAATAT ATCATCATGA ACAATAAAAC TGTCTGCTTA   3660

CATAAACAGT AATACAAGGG GTGTTATGAG CCATATTCAA CGGGAAACGT CTTGCTCGAG   3720

GCCGCGATTA AATTCCAACA TGGATGCTGA TTTATATGGG TATAAATGGG CTCGCGATAA   3780

TGTCGGGCAA TCAGGTGCGA CAATCTATCG ATTGTATGGG AAGCCCGATG CGCCAGAGTT   3840

GTTTCTGAAA CATGGCAAAG GTAGCGTTGC CAATGATGTT ACAGATGAGA TGGTCAGACT   3900

AAACTGGCTG ACGGAATTTA TGCCTCTTCC GACCATCAAG CATTTTATCC GTACTCCTGA   3960

TGATGCATGG TTACTCACCA CTGCGATCCC CGGGAAAACA GCATTCCAGG TATTAGAAGA   4020

ATATCCTGAT TCAGGTGAAA ATATTGTTGA TGCGCTGGCA GTGTTCCTGC GCCGGTTGCA   4080

TTCGATTCCT GTTTGTAATT GTCCTTTTAA CAGCGATCGC GTATTTCGTC TCGCTCAGGC   4140
```

```
GCAATCACGA ATGAATAACG GTTTGGTTGA TGCGAGTGAT TTTGATGACG AGCGTAATGG      4200

CTGGCCTGTT GAACAAGTCT GGAAAGAAAT GCATAAGCTT TTGCCATTCT CACCGGATTC      4260

AGTCGTCACT CATGGTGATT TCTCACTTGA TAACCTTATT TTTGACGAGG GGAAATTAAT      4320

AGGTTGTATT GATGTTGGAC GAGTCGGAAT CGCAGACCGA TACCAGGATC TTGCCATCCT      4380

ATGGAACTGC CTCGGTGAGT TTTCTCCTTC ATTACAGAAA CGGCTTTTTC AAAAATATGG      4440

TATTGATAAT CCTGATATGA ATAAATTGCA GTTTCATTTG ATGCTCGATG AGTTTTTCTA      4500

ATCAGAATTG GTTAATTGGT TGTAACACTG GCAGAGCATT ACGCTGACTT GACGGGACGG      4560

CGGCTTTGTT GAATAAATCG AACTTTTGCT GAGTTGAAGG ATCAGATCAC GCATCTTCCC      4620

GACAACGCAG ACCGTTCCGT GGCAAAGCAA AAGTTCAAAA TCACCAACTG GTCCACCTAC      4680

AACAAAGCTC TCATCAACCG TGGCTCCCTC ACTTTCTGGC TGGATGATGG GGCGATTCAG      4740

GCCTGGTATG AGTCAGCAAC ACCTTCTTCA CGAGGCAGAC CTCAGCGCCC CCCCCCCCT      4800

GCAGGTCGCC GAATGCCACG GCATCTCGCA ACCGTTCAGC GAACGCCTCC ATGGGCTTTT      4860

TCTCCTCGTG CTCGTAAACG GACCCGAACA TCTCTGGAGC TTTCTTCAGG GCCGACAATC      4920

GGATCTCGCG GAAATCCTGC ACGTCGGCCG CTCCAAGCCG TCGAATCTGA GCCTTAATCA      4980

CAATTGTCAA TTTTAATCCT CTGTTTATCG GCAGTTCGTA GAGCGCGCCG TGCGTCCCGA      5040

GCGATACTGA GCGAAGCAAG TGCGTCGAGC AGTGCCCGCT TGTTCCTGAA ATGCCAGTAA      5100

AGCGCTGGCT GCTGAACCCC CAGCCGGAAC TGACCCCACA AGGCCCTAGC GTTTGCAATG      5160

CACCAGGTCA TCATTGACCC AGGCGTGTTC CACCAGGCCG CTGCCTCGCA ACTCTTCGCA      5220

GGCTTCGCCG ACCTGCTCGC GCCACTTCTT CACGCGGGTG GAATCCGATC CGCACATGAG      5280

GCGGAAGGTT TCCAGCTTGA GCGGGTACGG CTCCCGGTGC GAGCTGAAAT AGTCGAACAT      5340

CCGTCGGGCC GTCGGCGACA GCTTGCGGTA CTTCTCCCAT ATGAATTTCG TGTAGTGGTC      5400

GCCAGCAAAC AGCACGACGA TTTCCTCGTC GATCAGGACC TGGCAACGGG ACGTTTTCTT      5460

GCCACGGTCC AGGACGCGGA AGCGGTGCAG CAGCGACACC GATTCCAGGT GCCCAACGCG      5520

GTCGGACGTG AAGCCCATCG CCGTCGCCTG TAGGCGCGAC AGGCATTCCT CGGCCTTCGT      5580

GTAATACCGG CCATTGATCG ACCAGCCCAG GTCCTGGCAA AGCTCGTAGA ACGTGAAGGT      5640

GATCGGCTCG CCGATAGGGG TGCGCTTCGC GTACTCCAAC ACCTGCTGCC ACACCAGTTC      5700

GTCATCGTCG GCCCGCAGCT CGACGCCGGT GTAGGTGATC TTCACGTCCT TGTTGACGTG      5760

GAAAATGACC TTGTTTTGCA GCGCCTCGCG CGGGATTTTC TTGTTGCGCG TGGTGAACAG      5820

GGCAGAGCGG GCCGTGTCGT TTGGCATCGC TCGCATCGTG TCCGGCCACG GCGCAATATC      5880

GAACAAGGAA AGCTGCATTT CCTTGATCTG CTGCTTCGTG TGTTTCAGCA ACGCGGCCTG      5940

CTTGGCCTCG CTGACCTGTT TTGCCAGGTC CTCGCCGGCG GTTTTTCGCT TCTTGGTCGT      6000

CATAGTTCCT CGCGTGTCGA TGGTCATCGA CTTCGCCAAA CCTGCCGCCT CCTGTTCGAG      6060

ACGACGCGAA CGCTCCACGG CGGCCGATGG CGCGGGCAGG GCAGGGGGAG CCAGTTGCAC      6120

GCTGTCGCGC TCGATCTTGG CCGTAGCTTG CTGGACCATC GAGCCGACGG ACTGGAAGGT      6180

TTCGCGGGGC GCACGCATGA CGGTGCGGCT TGCGATGGTT TCGGCATCCT CGGCGGAAAA      6240

CCCCGCGTCG ATCAGTTCTT GCCTGTATGC CTTCCGGTCA AACGTCCGAT TCATTCACCC      6300

TCCTTGCGGG ATTGCCCCGA CTCACGCCGG GGCAATGTGC CCTTATTCCT GATTTGACCC      6360

GCCTGGTGCC TTGGTGTCCA GATAATCCAC CTTATCGGCA ATGAAGTCGG TCCCGTAGAC      6420

CGTCTGGCCG TCCTTCTCGT ACTTGGTATT CCGAATCTTG CCCTGCACGA ATACCAGCTC      6480
```

```
CGCGAAGTCG CTCTTCTTGA TGGAGCGCAT GGGGACGTGC TTGGCAATCA CGCGCACCCC    6540

CCGGCCGTTT TAGCGGCTAA AAAAGTCATG GCTCTGCCCT CGGGCGGACC ACGCCCATCA    6600

TGACCTTGCC AAGCTCGTCC TGCTTCTCTT CGATCTTCGC CAGCAGGGCG AGGATCGTGG    6660

CATCACCGAA CCGCGCCGTG CGCGGGTCGT CGGTGAGCCA GAGTTTCAGC AGGCCGCCCA    6720

GGCGGCCCAG GTCGCCATTG ATGCGGGCCA GCTCGCGGAC GTGCTCATAG TCCACGACGC    6780

CCGTGATTTT GTAGCCCTGG CCGACGGCCA GCAGGTAGGC CGACAGGCTC ATGCCGGCCG    6840

CCGCCGCCTT TTCCTCAATC GCTCTTCGTT CGTCTGGAAG GCAGTACACC TTGATAGGTG    6900

GGCTGCCCTT CCTGGTTGGC TTGGTTTCAT CAGCCATCCG CTTGCCCTCA TCTGTTACGC    6960

CGGCGGTAGC CGGCCAGCCT CGCAGAGCAG GATTCCCGTT GAGCACCGCC AGGTGCGAAT    7020

AAGGGACAGT GAAGAAGGAA CACCCGCTCG CGGGTGGGCC TACTTCACCT ATCCTGCCCG    7080

GCTGACGCCG TTGGATACAC CAAGGAAAGT CTACACGAAC CCTTTGGCAA AATCCTGTAT    7140

ATCGTGCGAA AAAGGATGGA TATACCGAAA AAATCGCTAT AATGACCCCG AAGCAGGGTT    7200

ATGCAGCGGA AAAGATCCGA TCGTCAACGT TCACTTCTAA AGAAATAGCG CCACTCAGCT    7260

TCCTCAGCGG CTTTATCCAG CGATTTCCTA TTATGTCGGC ATAGTTCTCA AGATCGACAG    7320

CGTGTCACGG TTAAGCGAGA AATGAATAAG AAGGCTGATA ATTCGGATCT CTGCGAGGGA    7380

GATGATATTT GATCACAGGC AGCAACGCTC TGTCATCGTT ACAATCAACA TGCTACCCTC    7440

CGCGAGATCA TCCGTGTTTC AAACCCGGCA GCTTAGTTGC CGTTCTTCCG AATAGCATCG    7500

GTAACATGAG CAAAGTCTGC CGCCTTACAA CGGCTCTCCC GCTGACGCCG TCCCGGACTG    7560

ATGGGCTGCC TGTATCGAGT GGTGATTTTG TGCCGAGCTG CCGGTCGGGG AGCTGTTGGC    7620

TGGCTGGTGG CAGGATATAT TGTGGTGTAA ACAAATTGAC GCTTAGACAA CTTAATAACA    7680

CATTGCGGAC GTTTTTAATG TACCAAGCTT GCATGCCTGC AGSTCGAGTT ATTTTCAAAA    7740

AGCAGTATCG GCTAGAGCAT CAAGAAACTC GATTAAAAGT TTATCAAATG AAGCTGGAAA    7800

AGTCTTGACA GAGTTAGAAG ACATTAAAAT AGAGGTTGTG GAGTATTGTA AAAGAATTAT    7860

GCAAGCGCAA CCTACATGAC TAGTGGAGAT ATCATATGAC TACTTATCAG GGTTGGTGAA    7920

TTTTAAATAT TCCCAGACTG CTGCTAAAAC CTTAATGCAT CCAATTGGTG TTGACGAGAT    7980

GGCTATCCTG CTCAGTTTTT AATTGCTGCT TGGTCGATCT TGGAAATGAT TTATAATAG    8040

CAGTGCAGTC CTTCTTGATC TTTGGATGCA TGCCCAAAAG TGTTAAATCA ACTATTCTGA    8100

CTCTTGTTCC CAAAACAGAT GGTGCACAAA ATATGAAGGA GTTCATACTG ATAGCGTGAT    8160

GCAATCTTCT ATATTAAGTG ATATATAAGA TAATAGCAAA CCGGCTTAAA GTTACTTTAC    8220

AAGAGGCGAT GGAACCGAAT CAGAGCACCT TTGTGAAGGG GAGGCTCTTA CTAGAGAACA    8280

TATTTTAGC AACAAAACTA GTCAAGGACT ACCACAAGCA ATCACTCTCA TCTCGTTTAG    8340

CAATTAAGCT TGATATCTCT AAAGCGTTTG ACATAGAGCA ATGGCCGTTT ATTGCTGCTA    8400

GGCTACGTGT GATGGGTTAT CCATAGCTCT TTATACACTA GATAAATATA TGCATCTCTA    8460

CGTCCTCGTT TTGTTTTTTT CTCTAGCTCT TGTGGTATAA GGAAAGGATG CTCTCTTTCA    8520

CCGTACTTCT ATGTTATCAT CAACAATGTT TTGTCGACTA TGTTAAACAG AGCAGCTGTT    8580

ATGAAAGAGA TTGGTTCTCA CCCGTTTTGC AAGGAGATAA AGCTTACACA TCTTAGTTTT    8640

GCTGATGATA TTATGGTCTT CATGGATGGT ACTCTTGGTT CTCTCTGCAA CATCATGATA    8700

GTGGTTGATG AGTATGCCCA TATTTCAGTT TTTAACATCA ATGTGTCCAA GTCCACAATA    8760

TTTGATGCGG GTCGAGGGAA GATGACTTTG GAAATAGGGG CCACATCAGT AGGGTTAGTA    8820

GTAAGTTCTC TTCCCATTTG GTACCTTGGG CTGCGCTAAC CACAAAAGCA ATGACGAGAC    8880
```

```
TTGACTACAA ACCTCTACTT GACAAGATAA GGTCTCGTTT TTTAATTGGA CAAGCAAGCA    8940

CCTCTCACTT GAGGTTGTCT ACAACTTATG AACTCAGTTA TATGAAGCAT CTTAATTTTC    9000

TGGTGTTCAG TCTTCAGGCT TCCAAAAAAT GTTTTTAGAC ATTGAAAGGA GGTGTAGTTC    9060

ATTCCTCTAG AGTGGATCAT CGCTTGATGC AACTAAAGCA AAAGTGTCTT GGGAGGAGGT    9120

TTGCTACTCA AAAAAGGAAG GGGGCTTGGG GTTCCGCGTA TGATGGAGAT GTCTTTGATT    9180

TATGCGTTGA GCCTAATATG GAGGTTATAT ACCATGTCGG GCTCTCTATG GGTGGCATAG    9240

ATAAGTCATT ACCTTCTGCG CCAAGAATCA TTTTGGGATA TCAAAGCAAC GTCCTTAGGG    9300

TCTTCGGTTG GACGTAAGCT GCTCAAGCTT TGCCCACAAG CCATTGAGTT TATAAGAATG    9360

GAAGTAAAAG ATGGAGTTAA GACACGATCC TAGTCGGATA CTTGGTTGTC AATGGGGAGT    9420

CTTATTGATC GTAGTTGGAG AAAGGGGAAC ATATGAATTG GGAGTGCACC GAGATGCTAC    9480

AGTTGCAGAG GTTGTAGCAA GAGGTCACTG GTCAATCCGT CGTGGTCAGA ACCAACATAT    9540

AAGTTTGATT GTGGACCAGA TCATAGCTAA AGACCCGTCC GTACACTCGG CTAGTCAAGA    9600

TCATTGATTA GTATATATAC ATATTGTATT GCATGAAAAG TGTTTAAAGT AAATTGTGTC    9660

YTATACAAAG AATATATATR ACGATCATTG ATTAGTATAT ATACATATTG TATTGTGTGT    9720

TTAAAGTAAA TTGTGTCCTA TACAAAGAAT ATCTTTGTGG AGAAGCAAAG AGAATACATA    9780

CTTACGTAGG AATCTTTTTG TTTTCTTTTT TCAAAACGTA AGAATGTTTG CTTCCTTACA    9840

ATTCATACTT ATTAACTTAC ATATTATGTT TTCTTTTAAA TATTAAAAAT AACTAATTTT    9900

TATTAGGCAG CAAGTCATTT ACAAAGTAAA AAATTTCTGC CATGCATGTA ACCTTCATTT    9960

ATCATTCATT TTAGTTTGTA ACTTTTTATT AGATTTTGAT CAAGTTAACC GCTAAAATCT   10020

CATTTTATCC GTTCGCATTA AAGTTAAATA GATTGCTGAC ATATTTAAA TCTAATAGAA    10080

AATGCCATCT GGCAAATAAA CAACGGACAC GATTTTAAAC TAAATTTTAC CAAAAAGAAA   10140

AAACTTATAC GACTTTTCTT GCTTAGAAGT CTTTGCATTG TTAATAGATT GTTGAAAAGG   10200

TTTATTCATT ACTTTCATGC AGAGAGATAA CATATCATCG CGTGGGGATT TATTCAATCC   10260

AAAGAAAAGC TTCCAAAAAC TGACTYTGCT TCATGAAACA CTCACTCTAA TTTGCTTCAT   10320

CAATCTTAGG ACTGACTTTT CCAAATCAAT AATCCCGGSG AWCYATSTKC KMWTKKMCAW   10380

WGKKTTCGTG TTTTTTCGAA AGGAGACAAC TATCTTTTTA AAAGCTTTTC TATAGTGTGA   10440

TGACAAAAAA AAAATGTAAT TGTTAGTTGC AAAAGAAAAG TACAATAGTC TTTTCTAGTT   10500

TTGAGAGTTT AAGGTTTATG ATCGGAACTT AGAGTTTAAA TTTAAACTAT TTTGTTAATT   10560

TTTGGACTGA TAACAGTTTT TTTTTGAAAA TATTGAAACG TTGTTTACCT AATGTAACAT   10620

GTTATTCTAC TTAAATTACT TTATATTTTA ATAACATATA ATATTGAATA GGATATCATA   10680

GGATATTATT ACGTAATAAT ATCCTATGGT GTCATTTTAT AAGTTAGCAC AAGCTTGTTT   10740

TAACTTATAA AATGATTCTC CCTCCATATA AAAAGTTTG ATTTTATAGA ATGTTTATAC    10800

CGATTAAAAA AATAATAATG CTTAGTTATA AATTACTATT TATTCATGCT AAACTATTTC   10860

TCGTAACTAT TAACCAATAG TAATTCATCA AATTTTAAAA TTCTCAATTA ATTGATTCTT   10920

GAAATTCATA ACCTTTTAAT ATTGATTGAT AAAAATATAC ATAAACTCAA TCTTTTTAAT   10980

ACAAAAAAAC TTTAAAAAAT CAATTTTTCT GATTCGGAGG GAGTATATGT TATTGCTTAG   11040

AATCACAGAT TCATATCAGG ATTGGAAAAT TTTAAAGCCA GTGCATATCA GTAGTCAAAA   11100

TTGGTAAATG ATATACGAAG GCGGTACMAA ATTAGGTATA CTGGAGATAG GAGGACCCCC   11160

AAGTAGGTCG GTCACCTAGA GTTTTTCCAA TTAAACTGCG TATTAGTGTT TGGGAAAAAA   11220
```

```
AAACCAWRYS TMWRSCATGK CRGTATMGRT SMYCKKKWTT KTYTTTTTTT TTTTTTTTTT   11280

TCTTTTTGGA TAAATCTCAA TGGGTGATCT ATTGACTGTT TCTCTACGTC ACTATTTTAC   11340

TTACGTCATA GATGTGGCGG CATATATTCT TCAGGACTTT TCAGCCATAG GCAAGAGTGA   11400

TAGAGATACT CATATGCATG AAACACTAAG AAACAAATAA TTCTTGACTT TTTTTCTTTT   11460

ATTTGAAAAT TGACTGTAGA TATAAACTTT TATTTTTTCT GACTGTAAAT ATAATCTTAA   11520

TTGCCAAACT GTCCGATACG ATTTTTCTGT ATTATTTACA GGAAGATATC TTCAMAACAT   11580

TTTGAATGAA GTAATATATG AAATTCAAAT TTGAAATAGA AGACTTAAAT TAGAATCATG   11640

AAGAAAAAAA AACACAAAAC AACTGAATGA CATGAAACAA CTATATACAA TGTTTCTTAA   11700

TAAACTTCAT TTAGGGTATA CTTACATATA TACTAAAAAA ATATATCAAC AATGGCAAAG   11760

CTACCGATAC GAAACAATAT TAGGAAAAAT GTGTGTAAGG ACAAGATTGA CAMAAAAATA   11820

GTTACGAAAA CAACTTCTAT TCATTTGGAC AATTGCAATG AATATTACTA AAATACTCAC   11880

ACATGGACCA TGTATTTACA MAAACGTGAG ATCTATAGTT AACAAAAAAA AAAAAGAAAA   11940

AAATAGTTTT CAAATCTCTA TATAAGCGAT GTTTACGAAC CCCAAAATCA TAACACAACA   12000

ATAACCATTA TCAACTTAGA AAAATGGAAG ACGCCAAAAA CATAAAGAAA GGCCCGGCGC   12060

CATTCTATCC TCTDGAAGAT GGAACCGCTG GAGAGNCAAC TGCATAAGGC TATGAAGANG   12120

ATACGCCCTG GTTCCTGGAA CAATTGCTTT TACAGATGCA CATATCGAGG TGVACATCAC   12180

GTACGCNGAG TACTTCGAAA TGTCCGTTCG GTNNTGNGCA GAAGNNCTAT GAAACGANTA   12240

TGGGCTGAAT ACAAATCACA GAATCGTCGT ATGCAGTGAA AACTCTCTTC AATTCTTTAT   12300

GCCGGTGTTG GGCGCGTTAT TTATCGGAGT TGCAGTTGCG CCCGCGAACG ACATTTATAA   12360

TGAACGTGAA TTGCTCAACA GTATGRRCAT TTCGCAGCCT ACCGTRGTGT TYGTTTCCAA   12420

AAAGGGGTTG CAAAAAATTT TGAACGTGCA AAAAAARYTM CCAATMATCC ARAAAATTAT   12480

TATCATGGAT TCTAAAACGG ATTACCAGGG ATTTCAGTCG ATGTACACGT TCGTCACATC   12540

TCATCTACCT CCCGGTTTTA ATGAATACGA TTTTGTRCCA GAGTCCTTYG ATMGKGACAA   12600

RACAATTGCA CTGATMATGA AYTCCTCTGG ATCTACTGGK YTRCCTAARG GTGTSGCYCT   12660

KCCKCATAGA ACTGCCTGCG TSAGATTCTC GCATGCCAGA GATCCTATTT TTGGCAATCA   12720

AATCATTCCG GATACTGCGA TTTTAAGTGT TGTTCCATTC CATCACGGTT TTGGAATGTT   12780

TACTACACTC GGATATTTGA TATGTGGATT TCGAGTCGTC TTAATGTATA GATTTGAAGA   12840

AGAGCTGTTT YTRMGRWSCC TTCAGGATTA CAARATTCAA AGTGCGYTGC TRGTRCCAAC   12900

CCTATTYTCM TTCTTCGCCA AAAGCACTCT GATTGACAAA TACGATTTAT CTAATTTACA   12960

CGAAATTGCT TCTGGKGGCG CWCCYCTYTC KAARGAAGTC GGGGAAGCGG TTGCMAARMG   13020

STTCCATCTK CCAGGKATMM GRCAAGGATA TGGGCTCACT GAGACTACAT CAGCTATTCT   13080

GATTACACCC GAGGGGGATG ATAAACCGGG CGCGGTCGGT AAAGTTGTTC CATTTTTTGA   13140

AGCGAAGGTT GTGGATCTGG ATACCGGGAA AACGCTGGGC GTTAATCARA GAGGCGAAYT   13200

RTGTGTSAGA GGWCCTATGA TTATGTCCGG TTATGTAAAC AATCCGGAAG CGACCAACGC   13260

CTTGATTGAC AAGGATGGAT GGCTACATTC TGGAGACATA GCTTACTGGG ACGAAGACGA   13320

ACACTTCTTC ATMGTTGACC GCYTGAAGTC TYTRATTAAR TACAAAGGMT ATCAGGTGGC   13380

YCCCGCTGAA TTGGAATCSA TMTTGYTMCA ACACCCCAAC ATCTTCGACG CRGGYGTSGC   13440

AGGTCTTCCC GACGATGACG CCGGTGAACT TCCCGCCGCC GTTGTTGTTT TGGAGCACGG   13500

AAAGACGATG ACGGAAAAAG AGATCGTGGA TTACGTCGCC AGTCAAGTAA CAACCGCGAA   13560

AAAGTTGCGC GGAGGAGTTG TGTTTGTGGA CGAAGTACCG AAAGGTCTTA CCGGAAAACT   13620
```

-continued

```
CGACGCAAGA AAAATCAGAG AGATCCTCAT AAAGGCCAAG AAGGGCGGAA AGWYCRMMKT  13680

GTAAAATGTA ACTGTATTCA GCGATGACGA AATTCTTAGC TATTGTAATA TTATATGCAA  13740

ATTGATGAAT GGTAATTTTG TAATTGTGGG TCACTGTACT ATTTTAACGA ATAATAAAAT  13800

CAGGTATAGG TAACTAAAAA GGAATTCGAG CTCGAATTCC CGATCTAGTA ACATAGATGA  13860

CACCGCGCGC GATAATTTAT CCTAGTTTGC GCGCTATATT TTGTTTTCTA TCGCGTATTA  13920

AATGTATAAT TGCGGGACTC TAATCATAAA AACCCATCTC ATAAATAACG TCATGCATTA  13980

CATGTTAATT ATTACATGCT TAACGTAATT CAACAGAAAT TATATGATAA TCATCGCAAG  14040

ACCGGCAACA GGATTCAATC TTAAGAAACT TTATTGCCAA ATGTTTGAAC GATCGGGGAT  14100

CGATCCCGTG GCG                                                    14113
```

MUTANT PLANTS AND USES THEREFOR

This application is a divisional of application Ser. No. 08/992,801, filed Dec. 18, 1997, now U.S. Pat. No. 6,107,544 which is a continuation-in-part of application Ser. No. 08/648,949, filed May 16, 1996, now U.S. Pat. No. 5,792,904, issued Aug. 11, 1998, which is a continuation-in-part of application Ser. No. 08/165,238, filed Dec. 10, 1993, abandoned, which is a continuation-in-part of application Ser. No. 08/002,285, filed Jan. 8, 1993, abandoned. The complete disclosures of each of these parent applications are incorporated herein by reference.

FIELD OF THE INVENTION

The present invention relates to disease resistance in plants, particularly identifying and breeding disease resistance into plants based on constitutive expression of genes associated with systemic acquired resistance (SAR).

BACKGROUND OF THE INVENTION

Plants are constantly challenged by a wide variety of pathogenic organisms including viruses, bacteria, fungi, and nematodes. Crop plants are particularly vulnerable because they are usually grown as genetically uniform monocultures; when disease strikes, losses can be severe. However, most plants have their own innate mechanisms of defense against pathogenic organisms. Natural disease resistance genes often provide high levels of resistance to or immunity against pathogens.

Systemic acquired resistance (SAR) is one component of the complex system plants use to defend themselves from pathogens (Hunt and Ryals, *Crit. Rev. in Plant Sci.* 15, 583–606 (1996); Ryals et al., *Plant Cell* 8, 1809–1819 (1996); and U.S. Pat. No. 5,614,395; each of which is incorporated herein by reference). SAR is a particularly important aspect of plant pathogen responses because it is a pathogen-inducible, systemic resistance against a broad spectrum of infectious agents, including viruses, bacteria, and fungi. When the SAR signal transduction pathway is blocked, plants become more susceptible to pathogens that normally cause disease, and they also become susceptible to some infectious agents that would not normally cause disease (Gaffney et al., *Science* 261, 754–756 (1993); Delaney et at., *Science* 266, 1247–1250 (1994); Delaney et al., *Proc. Natl. Acad. Sci. USA* 92, 6602–6606 (1995); Delaney, *Plant Phys.* 113, 5–12 (1997); Bi et al., *Plant J.* 8, 235–245 (1995); and Mauch-Mani and Slusarenko, *Plant Cell* 8, 203–212 (1996); each of which is incorporated herein by reference). These observations indicate that the SAR signal transduction pathway is critical for maintaining plant health.

Conceptually, the SAR response can be divided into two phases. In the initiation phase, a pathogen infection is recognized and a signal is released that travels through the phloem to distant tissues. This systemic signal is perceived by target cells, which react by expression of both SAR genes and disease resistance. The maintenance phase of SAR refers to the period of time, from weeks up to the entire life of the plant, during which the plant is in a quasi steady state and disease resistance is maintained (Ryals et al., 1996).

Associated with the onset of SAR is the expression of a set of genes called SAR genes, many of which belong to the family of pathogenesis-related (PR) proteins. A protein is classified as an SAR protein when its presence or activity correlates tightly with maintenance of SAR (Neuenschwander et al., *Plant-Microbe Interactions*, Vol. 1, G. Stacey & N. T. Keen, eds. (New York, N.Y.: Chapman and Hall), pp. 81–106 (1996), incorporated herein by reference). These proteins represent markers for SAR in a sense that SAR is not found in the absence of SAR proteins. PR proteins are induced in large amounts in response to infection by various pathogens, including viruses, bacteria and fungi. Some of these proteins have a role in providing systemic acquired resistance to the plant. Pathogenesis-related proteins were first discovered in tobacco plants (*Nicotiana tabacum*) reacting hypersensitively to infection with tobacco mosaic virus (TMV). Subsequently, PR proteins have been found in many plant species (See, for example, Redolfi et al. (1983) *Neth J Plant Pathol* 89:245–254; Van Loon (1985) *Plant Mol. Biol.* 4:111–116; and Uknes et al. (1992) *Plant Cell* 4:645–656; all of which are incorporated herein by reference.) Such proteins are believed to be a common defensive systemic response of plants to infection by pathogens. Pathogenesis-related proteins include, but are not limited to, SAR8.2 proteins, acidic and basic forms of tobacco PR-1a, PR-1b, and PR-1c, PR-1', PR-2, PR-2', PR-2", PR-N, PR-O, PR-O', PR-4, PR-P, PR-Q, PR-S, and PR-R proteins, cucumber peroxidases, the chitinase which is a basic counterpart of PR-P or PR-Q, and the beta-1,3-glucanase (glucan endo-1,3-beta-glucosidase, EC 3.2.1.39) which is a basic counterpart of PR-2, PR-N or PR-O, and the pathogen-inducible chitinase from cucumber. See, for example, Ward et al. (1991) *Plant Cell* 3, 1085–1094, incorporated herein by reference. See also, Uknes et al. (1992); and U.S. Pat. No. 5,614,395. Transgenic disease-resistant plants have been created by transforming plants with various SAR genes, including PR protein genes (U.S. Pat. No. 5,614,395).

Salicylic acid (SA) accumulation appears to be required for SAR signal transduction. Plants that cannot accumulate SA due to treatment with specific inhibitors, epigenetic repression of phenylalanine ammonia-lyase, or transgenic expression of salicylate hydroxylase, which specifically degrades SA, also cannot exhibit either SAR gene expression or disease resistance (Gaffney et al., 1993; Delaney et al., 1994; Mauch-Mani and Slusarenko 1996; Maher et al., *Proc. Natl. Acad. Sci. USA* 91, 7802–7806 (1994), incorporated herein by reference; Pallas et al., *Plant J.* 10, 281–293 (1996), incorporated herein by reference). Although it has been suggested that SA might serve as the systemic signal, this is currently controversial and, to date, all that is known for certain is that if SA cannot accumulate, then SAR signal transduction is blocked (Pallas et al., 1996; Shulaev et al., *Plant Cell* 7, 1691–1701 (1995), incorporated herein by reference; Vernooij et al., *Plant Cell* 6, 959–965 (1994), incorporated herein by reference).

Recently, Arabidopsis has emerged as a model system to study SAR (Uknes et al. (1992); Uknes et al., *Mol. Plant-Microbe Interact.* 6, 692–698 (1993); Cameron et al., *Plant J.* 5, 715–725 (1994); Mauch-Mani and Slusarenko, *Mol. Plant-Microbe Interact.* 7, 378–383 (1994); Dempsey and Klessig, *Bulletin de L'Institut Pasteur* 93, 167–186 (1995); all of which are incorporated herein by reference). It has been demonstrated that SAR can be activated in Arabidopsis by both pathogens and chemicals, such as SA, 2,6-dichloroisonicotinic acid (INA) and benzo(1,2,3)thiadiazole-7-carbothioic acid S-methyl ester (BTH) (Uknes et al., 1992; Vernooij et al., *Mol. Plant-Microbe Interact.* 8, 228–234 (1995), incorporated herein by reference; Lawton et al., *Plant J.* 10, 71–82 (1996), incorporated herein by reference). Following treatment with either INA or BTH or pathogen infection, at least three PR protein genes, namely, PR-1, PR-2, and PR-5 are coordinately induced concomitant with the onset of resistance (Uknes et al., 1992, 1993).

While there have therefore been advances in plant genetic engineering, the prospects for the general use of these techniques for plant improvement are tempered by the realization that relatively few genes corresponding to plant traits of interest have been identified or cloned. Further, traits of interest often involve multi-gene families. Selection for plants carrying pathogen or disease resistance genes is thus laborious and time consuming. There is therefore needed a method to identify plants expressing resistance genes for use in plant breeding programs.

SUMMARY OF THE INVENTION

The present invention is drawn to methods for breeding disease resistance or resistance to pathogens into plants. Lesion or disease mimic mutants can be utilized to identify plants having desired traits such as a disease resistant phenotype. This method involves selecting disease lesion mimic mutants based on either resistance to a pathogen of interest or on the expression of systemic acquired resistance (SAR) genes. Such mutants having the desired traits or expressing the desired genes are then used in breeding programs.

Additionally, plants for use in a breeding program can be selected based on constitutive expression of SAR genes. That is, visible phenotypically normal plants that constitutively express SAR genes can be utilized. Progeny are screened for either resistance to a pathogen of interest or for the expression of systemic acquired resistance genes. Because these mutants have a significant level of disease resistance and no apparent negative phenotype, they have utility in breeding crop plants with constitutive, hereditary disease resistance. As an alternative to assaying on the basis of SAR gene expression, it is also possible to use a line transformed with a reporter gene such as luciferase under the regulation of an SAR gene promoter such as the PR-1a promoter as a stock line in which to generate new mutants; constitutive expressors of the reporter gene also therefore constitutively express SAR genes.

The invention is further drawn to the selection and utilization of plant mutants that do not express systemic acquired resistance genes, even when induced by a pathogen. Such non-inducible immunity mutants, which have a universal disease susceptible phenotype, have utility in disease and pathogenesis testing and fungicide screening programs.

DEFINITIONS

For clarity, certain terms used in the specification are defined and presented as follows:

cim: constitutive immunity phenotype. Also refers to disease resistant mutant plants having this phenotype in the absence of lesions (a.k.a. cim Class II).

cim Class I: class of mutants characterized by having lesions, high constitutive salicylic acid levels, and high constitutive levels of SAR gene expression. Also referred to as lsd mutants.

cim Class II: class of mutants characterized by having high constitutive salicylic acid levels and high constitutive levels of SAR gene expression, but no lesions. Also referred to as cim mutants.

cim Class III: class of mutants characterized by having high constitutive levels of SAR gene expression, but without lesions and without high constitutive salicylic acid levels.

lsd: lesion simulating disease phenotype. Also refers to disease resistant mutant plants having this lesion mimic phenotype (a.k.a. cim Class I).

nim: non-inducible immunity phenotype. Also refers to mutant plants having a universal disease susceptible phenotype, in which SAR can not be activated by conventional biological and chemical activators of SAR.

DETAILED DESCRIPTION OF THE INVENTION

Disease Resistant Mutants

The present invention relates to nontransgenic mutant plants that have an enhanced response to pathogen infection and therefore have a disease resistant phenotype. In one embodiment, the lesion mimic phenotype is used as a tool to identify plants having desired traits or expressing genes of interest. In another embodiment, constitutive expression of SAR genes in the absence of a lesion mimic phenotype is used to select disease resistant mutants. In yet another embodiment, constitutive expression of SAR genes in the absence of a lesion mimic phenotype and the absence of increased salicylic acid levels (an endogenous signal for SAR) may be used to select disease resistant mutants.

Thus, mutant plants that display enhanced disease resistance fall into three broad classes. The first class consists of mutant plants that display spontaneous lesion formation in the absence of pathogen attack and mount an SAR response concomitant with cell death. Presumably, spontaneous necrosis triggers activation of SAR in these mutants. This class of mutants has been designated as lsd mutants (lsd= Lesion Simulating Disease), which are also referred to herein as "cim Class I" mutants. lsd (aka cim Class I) mutants form spontaneous lesions on the leaves, have high constitutive salicylic acid levels (an endogenous signal for SAR), have high levels of PR-1, PR-2 and PR-5 mRNA, and are resistant to fungal and bacterial pathogens. (See, for example, Dietrich et al. (1994) and Weymann et al. (1995)).

Lesions are a hypersensitive reaction characterized by a local necrosis of the tissues immediately surrounding the infection site of the pathogen and a subsequent localization of the pathogen, which is in contrast to a sensitive reaction wherein the pathogen spreads throughout the plant. Lesion mimic mutants exhibit the hypersensitive reaction without having had any contact with a pathogen. Lesion mimic mutants are widely known in plants. Such lesion mimic mutants may be obtained from mutagenesis or by spontaneous mutation. In fact, both spontaneous and mutagen-induced cases of dominant and recessive mutants causing discrete leaf lesion formation have been reported in a number of plants including maize, tomato, wheat, tobacco, barley, sunflower, cucumber, etc. See, for example, Neuffer and Calvert (1975) *The Journal of Heredity* 66:265–270; Cameron J. W. (1964) *Maize Genet. Coop. News Letter* 38:32–33; Gardner C. O. (1971) *Maize Genet. Coop. News Letter* 45:150; Hornbrook and Gardner (1970) *Rad. Botany* 10:113–117; Simmonds N. W. (1950) *Maize Genet. Coop. News Letter* 24:26–27; and Walbot et al. (1983) in *Genetic Engineering of Plants*, Kosuge et al. (eds.) Plenum Publishing Corporation. However, the present invention is the first to recognize that the lesion mimic phenotype is associated with SAR and the expression of pathogenesis-related proteins and that the expression of SAR genes can be separated from the lesion phenotype.

The second class of disease resistant mutants consists of plants that display constitutive SAR gene expression and pathogen resistance in the absence of spontaneous lesion formation. This class of mutants has been designated as cim mutants (cim=Constitutive IMmunity), which are also referred to herein as "cim Class II" mutants. cim mutants have all the characteristics of lsd mutants except spontaneous lesions. As an example, the cim3 mutant line described below in the experimental section falls into this cim class (aka cim Class II) and is a dominant mutation with wild-type appearance that expresses stable, elevated levels of SA, SAR gene mRNA, and has broad spectrum disease resistance. cim mutants may be obtained from mutagenesis or by spontaneous mutation.

The third class consists of mutants that display constitutive SAR gene expression and pathogen resistance in the absence of spontaneous lesion formation and in the absence of increased levels of salicylic acid accumulation.

The table below illustrates the characteristics of the three classes of disease resistant mutant plants.

| ATTRIBUTE | cim Class I | cim Class II | cim Class III |
|---|---|---|---|
| Lesion[1] | + | − | − |
| SA[2] | + | + | − |
| SAR Gene Expression[3] | + | + | + |

[1] The presence +, or absense −, of the Lesion Mimic phenotype
[2] Salicylic Acid detected
[3] As measured by RNA gel blot analysis Because SAR or SAR-like genes are expressed in all plant species exhibiting systemic acquired resistance, expression of such genes can be determined by probing with known SAR DNA sequences. See, for example, Lawton et al. (1993) "The molecular biology of systemic acquired resistance" in *Mechanisms of Defence Responses in Plants*, B. Fritig and M. Legrand, eds. (Dordrecht, The Netherlands: Kluwer Academic Publishers), pp. 422–432, incorporated by reference herein in its entirety; Uknes et al. (1992) *Plant Cell* 4:645–656; and Ward et al. (1991) *Plant Cell* 3:1085–1094. Methods for hybridization and cloning are well known in the art. See, for example, *Molecular Cloning, A Laboratory Manual*, 2nd Edition, Vol. 1–3, Sambrook et al. (eds.) Cold Spring Harbor Laboratory Press (1989) and the references cited therein. Alternatively, such SAR or SAR-like genes can be found by other methods such as protein screening, +/− screening, etc. See, for example, U.S. Pat. No. 5,614,395; Liang and Pardee (1992) *Science* 257:967–971; and St. John and Davis (1979) *Cell* 16:443; herein incorporated by reference.

The present invention recognizes that SAR genes are constitutively expressed in some lesion mimic mutant plants (lsd mutants). Furthermore, the lesion mimic phenotype can be separated from expression of the SAR genes. Therefore, lesion mimic mutants expressing SAR genes can be utilized in breeding programs. Progeny can be selected based on expression of the SAR genes or resistance to pathogens and a desired phenotype. This method offers a source of resistance to pathogens for use in breeding programs. The present invention further recognizes that SAR genes may be constitutively expressed in plants that do not exhibit any lesion formation or necrosis (cim mutants); that is, plants that display a normal phenotype. Such plants can also be used in breeding programs.

As set forth below in the examples, a high-throughput Northern blot screen was developed to identify mutant plants having high concentrations of PR-1 mRNA during normal growth, with the idea that these mutants also exhibit systemic acquired resistance. A number of mutants have been isolated using this screen and they have been shown to accumulate not only PR-1 but also PR-2 and PR-5 mRNAs (Lawton et al. (1993); Dietrich et al. (1994); and Weymann et al. (1995)). These mutants also have elevated levels of SA and are resistant to pathogen infection, confirming that this approach can be used to isolate SAR signal transduction mutants. Both cim Class I (lsd) and cim Class II (cim) mutants have been isolated using this screen.

As an alternative to assaying on the basis of SAR gene expression, it is possible to use a line transformed with a reporter gene such as luciferase under the regulation of an SAR gene promoter such as the PR-1a promoter as stock line in which to generate new mutants; mutants that constitutively express SAR genes therefore also constitutively express the reporter gene. As described below in the examples, transgenic plant lines harboring a chimeric PR-1 promoter/luciferase (PR-1/uc) construct were developed. Following treatment of these lines with either chemical activators of SAR or incompatible pathogens, luciferase activity was induced several thousand fold concomitant with induction of PR-1 expression. In PR-1/luc plants, biological induction of SAR gene expression can be followed by detection of light emission. This was shown by treatment of one PR-1/luc line with turnip crinkle virus (TCV) leading to a hypersensitive response. Nine days after TCV inoculation, in vivo monitoring of photon emission revealed that all untreated leaves displayed elevated levels of luciferase activity.

To isolate mutants that displayed constitutive SAR in the absence of spontaneous cell death, seeds of PR-1/luc plants were mutagenized. $M_2$ progeny were screened for constitutive luciferase activity in vivo, and 605 potential mutants were isolated. 249 of these mutations were lethal, and 266 mutants displayed visible lesion formation. Upon analysis of the 90 remaining mutants in the next generation, trypan blue staining revealed that 74 of them were lsd class mutants and 16 of them were cim class mutants. Both classes of mutants exhibited elevated levels of salicylic acid, constitutive SAR gene expression, and increased resistance to pathogens such as *Peronospora parasitica*.

The PR-1/luciferase reporter system was chosen because luciferase activity can be monitored in vivo without affecting the integrity of the plant. This feature opens up the possibility to perform rapid examination of many plants as well as to reexamine the same tissue several times throughout an experiment (Millar et al., (1992) *Plant Mol. Biol. Rep.* 10, 324–337). Interestingly, the in planta pool of luciferase protein can be inactivated by treatment with luciferin. This facilitates the study of luciferase transcription over a defined time period, regardless of the luciferase pool present before treatment with luciferin (Millar et al., 1992). Also, luciferase activity can easily be reexamined in vitro providing the means for fast confirmation of results obtained by in vivo monitoring.

Three lines of evidence correlate light emission by PR-1/luc plants with SAR-gene expression:
  (i) Treatment with chemical activators of SAR gene expression induces luciferase activity in vivo and in vitro as well as PR-1 mRNA levels with similar kinetics.
  (ii) Infection of PR-1/luc plants with a biological inducer activates luciferase activity and PR-1 gene expression in both local and systemic tissue.
  (iii) Mutants identified by in vivo monitoring of constitutive luciferase activity display both constitutive SAR gene expression (PR-1, PR-2 and PR-5) and enhanced resistance to *P. parasitica*.

Taken together, these results indicate that in PR-1/luc plants, in vivo monitoring of luciferase activity provides a method for detection of the onset of SAR in these plants.

Once plants that constitutively express SAR genes are selected, for example, by one of the above-described screening methods, they can be utilized in breeding programs to incorporate constitutive expression of the SAR genes and resistance to pathogens of interest into plant lines. Progeny for further crossing are selected based on expression of the SAR genes and disease resistance as well as for other characteristics important for production and quality.

Pathogens of interest include but are not limited to viruses or viroids, e.g. tobacco or cucumber mosaic virus, ringspot virus or necrosis virus, pelargonium leaf curl virus, red clover mottle virus, tomato bushy stunt virus, and like viruses; fungi, e.g. *Phytophthora parasitica, Peronospora tabacina*, etc.; bacteria, e.g. *Pseudomonas syringae, Pseudomonas tabaci*, etc.; insects, such as aphids e.g. *Myzus persicae*; nematodes, e.g. *Meloidogyne incognita*; lepidoptera, e.g. Heliothus spp. etc. The methods of the invention are useful against a number of disease organisms of maize including but not limited to downy mildews such as *Scleropthora macrospora, Sclerophthora rayissiae, Sclerospora graminicola, Peronosclerospora sorghi, Peronosclerospora philippinensis, Peronosclerospora sacchari, Peronosclerospora maydis*; rusts such as *Puccinia sorphi, Puccinia polysora, Physopellazeae*; other fungi such as *Cercospora zeae-maydis, Colletotrichum graminicola, Fusarium monoliforme, Exserohilum turcicum, Bipolaris maydis*; and bacteria such as *Erwinia stewartii*.

The present invention avoids the screening of a large amount of material, including world collections and related species, generally necessary to identify usable resistance genes. Instead the methods described herein may be used to identify plants that potentially express resistance genes.

Accordingly, lsd or cim mutants of a plant of interest are selected and tested for resistance to a pathogen of interest or alternatively for constitutive expression of SAR genes. Such mutants are then used in breeding programs to introduce the resistance trait into breeding lines. That is, the constitutive expression of the SAR genes is introduced into plants. Such constitutive expression of the SAR genes is associated with immunity to pathogens.

Following the use of the selected lesion mutant or plant that constitutively expresses SAR genes in the breeding program, the resistance trait is incorporated into plant lines through breeding in combination with other characteristics important for production and quality. Breeding approaches and techniques are known in the art. See, for example, Welsh J. R., *Fundamentals of Plant Genetics and Breeding*, John Wiley & Sons, NY (1981); *Crop Breeding*, Wood D. R. (Ed.) American Society of Agronomy Madison, Wis. (1983); Mayo O., *The Theory of Plant Breeding*, Second Edition, Clarendon Press, Oxford (1987); Singh, D. P., *Breeding for Resistance to Diseases and Insect Pests*, Springer-Verlag, NY (1986); and Wricke and Weber, *Quantitative Genetics and Selection in Plant Breeding*, Walter de Gruyter and Co., Berlin (1986).

Disease resistant mutants have been reported in a variety of plants including but not limited to maize, tomato, wheat, Arabidopsis, oats, tobacco, sunflower, cucumber, etc. Accordingly, the invention can be used in breeding any plant in which disease resistant mutants can be found or induced through mutagenesis. Methods are known in the art for mutagenesis and selection.

Universal Disease Susceptible Mutants

The present invention further relates to nontransgenic mutants that are defective in their normal response to pathogen infection in that they do not express genes associated with systemic acquired resistance. These mutants are referred to as nim mutants (for non-inducible immunity) and are useful as "universal disease susceptible" (UDS) plants by virtue of their being susceptible to many strains and pathotypes of pathogens of the host plant and also to pathogens that do not normally infect the host plant, but that normally infect other hosts. They can be selected by treating seeds or other biological material with mutagenic agents and then selecting progeny plants for the UDS phenotype by treating progeny plants with known chemical inducers (e.g. INA) of the systemic acquired response and then infecting the plants with a known pathogen. Non-inducible mutants develop severe disease symptoms under these circumstances, whereas non-mutants are induced by the chemical compound to systemic acquired resistance. nim mutants can be equally selected from mutant populations generated by chemical and irradiation mutagenesis, as well as from populations generated by T-DNA insertion and transposon-induced mutagenesis. Techniques of generating mutant plant lines are well known in the art.

As SAR and SAR gene expression is a phenomenon ubiquitous to plants in general, nim mutants can be generated from any plant species. Disease susceptible plants incapable of expressing SAR genes have been created by transforming various species with the nahG gene. As set forth above, the nahG gene encodes salicylate hydroxylase, which specifically degrades SA. Without SA, NahG plants cannot express SAR genes and exhibit SAR in response to pathogen infection or chemical induction, both of which normally activate SAR (Gaffney et al., 1993). Thus, nahG effectively blocks the SAR pathway. The nim mutation also blocks the SAR pathway. Thus, like NahG plants, universal disease susceptible nim mutants that also are incapable of expressing SAR genes are not limited to any particular plant species.

nim mutants provide useful indicators of the evaluation of disease pressure in field pathogenesis tests where the natural resistance phenotype of so-called wild-type (i.e. non-mutant) plants may vary and therefore not provide a reliable standard of susceptibility. Furthermore, nim plants have additional utility for the testing of candidate disease resistance transgenes. Using a nim stock line as a recipient for transgenes, the contribution of the transgene to disease resistance is directly assessable over a base level of susceptibility. Furthermore, the nim plants are useful as a tool in the understanding of plant-pathogen interactions. nim host plants do not mount a systemic response to pathogen attack, and the unabated development of the pathogen is an ideal system in which to study its biological interaction with the host.

As nim host plants may also be susceptible to pathogens outside of the host-range they normally fall, these plants also have significant utility in the molecular, genetic, and biological study of host-pathogen interactions. Furthermore, the UDS phenotype of nim plants also renders them of utility for fungicide screening. nim mutants selected in a particular host have considerable utility for the screening of fungicides using that host and pathogens of the host. The advantage lies in the UDS phenotype of the mutant, which circumvents the problems encountered by hosts being differentially susceptible to different pathogens and pathotypes, or even resistant to some pathogens or pathotypes.

nim mutants have further utility for the screening of fungicides against a range of pathogens and pathotypes using a heterologous host i.e. a host which may not normally be within the host species range of a particular pathogen. Thus, the susceptibility of nim mutants of Arabidopsis (which is an easily manipulatable species and has limited space requirements) to pathogens of other species (e.g. crop plant species) would facilitate efficacious fungicide screening procedures for compounds against important pathogens of crop plants.

Gene Mapping

After lesion mimic mutants, phenotypically normal mutant plants constitutively expressing SAR genes, or universal disease susceptible mutants have been identified, further analysis can be performed to yield information that is useful in breeding programs. For example, restriction fragment length polymorphisms (RFLP) associated with the expression of the SAR genes and resistance can be identified. Once at least one RFLP associated with disease resistance or susceptibility is determined, this RFLP can then be used to screen for the presence of the resistance or susceptible phenotype. RFLPs are valuable to plant breeders to identify genes affecting agronomic traits on the plant genome through the identification of linked genetic markers. Genetic linkage analysis between DNA polymorphisms and traits of agronomic importance is useful to identify agronomically important genes, to classify inbreds, hybrids and breeding populations according to their genes, and then more effectively incorporate these genes into improved inbreds and hybrids.

RFLPs associated with disease resistance are potentially of great value to breeders. Therefore, the invention encompasses analyzing chromosomes to identify DNA polymorphisms linked with the lesion mimic phenotype and with expression of SAR genes. To practice one aspect of the invention, the lesion mutant phenotype may be used as the phenotype associated with disease resistance. RFLPs can then be found that are associated with the lesion phenotype and disease resistance. Similarly, RFLPs can be found that are associated with the cim and nim phenotypes. The RFLP can then be used in a breeding program of choice. The identified genetic linkages between specific probes and genetic components of agronomically important traits are used as an aid in selecting plants and populations in "classical" plant breeding based on Mendelian genetics.

Methods for determining RFLPs and the identification of polymorphisms associated with particular traits are known in the art. See, for example, Burr et al. (1983), "The application of restriction fragment length polymorphism to plant breeding", in *Genetic engineering principles and methods*, Vol. 5 (eds. J. D. Selow & A. Hollaender) pp. 45–59, New York, Plenum Press; Helentjaris T. (1987) *Trends in Genetics* 3:217–221; Helentjaris et al. (1985) *Plant Mol. Biol.* 5:109–118; WO 89/07647; EP 0317239; and EP 0306139.

In a typical method to identify a polymorphism according to the invention, DNA is extracted from the plant cell and digested with a given restriction endonuclease. After the digest is obtained, and the digested DNA is separated by standard techniques such as agarose gel electrophoresis, the separated bands are probed with a DNA fragment coding for the RFLP sequence.

Probes must be found to detect a polymorphism if it is to be useful for testing linkage to the desired trait. The polymorphism must be found to be linked to genes affecting traits or to other useful markers in studies, or to be immediately adjacent to pre-existing markers. The particular probe can be of any desired sequence length as long as it is capable of identifying the polymorphism in the involved DNA region or locus.

Methods for generating additional new DNA fragments also linked with the gene for a particular trait are as follows. A first method is to test randomly chosen DNA fragments that map to the appropriate region of the genomic map. Such mapping can be achieved by in situ hybridization to metaphase chromosome spreads or by genetic linkage to any marker already mapped to the region.

Additional DNA probes may be obtained by constructing a library from DNA isolated from metaphase chromosomes. Such chromosomes may be sorted, for example on a fluorescence activated cell sorter.

Finally, new DNA probes may be obtained from the region of the chromosome containing the agronomically important gene by using any probes already mapped to the region to "fish out" adjacent overlapping pieces of DNA from genomic libraries (chromosome walking).

Other methods for the identification of markers linked to disease-resistance genes are known in the art and can be used in the present invention. Such methods include, but are not limited to segregant analysis as a method for rapidly identifying markers (Michelmore et al. (1991) *Proc. Natl. Acad. Sci. USA* 88:9828–9832, herein incorporated by reference), and the use of RAPD (random amplified polymorphic DNAs) as described by Williams et al. (1990) *Nucleic Acids Res.* 18:6531–6535, herein incorporated by reference.

Methods for labeling the DNA probes and for hybridization are known in the art. See, for example, Sambrook et al. (1989).

Gene Cloning

The genes responsible for SAR gene expression and the lesion mimic trait in the lsd mutants, the genes responsible for SAR gene expression in the cim mutants, as well as the gene responsible for the nim mutant phenotype can be cloned and the corresponding cDNAs reintroduced into transgenic plants in either sense or antisense orientation to modify plant phenotype.

The cloning of the lsd, cim, and nim mutation genes can be undertaken using techniques well known in the art. Markers that are located close to the mutation of interest can be identified such as by using RFPL and RAPD technology. Typically this is done in a segregating population such as the F2 generation derived from a cross between a homozygous mutant and homozygous non-isogenic race, but alternatively it can be done in anther cultured dihaploid lines derived from a heterozygote individual. Once markers have been identified that co-segregate with the desired phenotype, the adjacent DNA can be cloned directly using the markers as probes in a genomic library screen coupled with subsequent "genome walking" to the desired destination. This step can be facilitated using YAC cloning techniques, which enable the subcloning of larger genomic fragments than is possible using traditional lambda phage or cosmid cloning techniques. The target sequence is precisely identified from its reintroduction from such a subclone into a host plant; depending on whether the mutant phenotype is dominant or recessive, the reintroduction assay can be completed in the wild-type in primary transformants, or subsequent segregating generations. Having successfully cloned the mutant gene, the wild-type gene is easily clonable using the mutant gene as a probe in a library screen. "Map-based cloning technology", as it is known in the art, is well within the competence of one of ordinary skill in the art and is described, for example, in Arondel et al. (*Science* 258: 1353–1358 (1992)) and Martin et al. (*Science* 262: 1432–1436 (1993)). Recently, the gene responsible for nim mutant phenotype was cloned (Ryals et al. (1997) *Plant Cell* 9, 425–439, incorporated herein by reference) and was shown to share strong homology with the IκB class of mammalian transcription regulators.

As the inventors have established the existence and utility of the lesion mimic and nim mutations described in this specification, it will be apparent to those of ordinary skill in the art that the same types of mutation can be remade using insertion mutagenic techniques, which thus facilitate the subsequent cloning of the target gene of interest. Examples of insertion mutagenic techniques that are particularly useful in the context of cloning genes from plants include the T-DNA insertion technique in which the T-DNA from Agrobacterium is inserted randomly into the genome, and transposon insertion mutagenesis, where a natural or introduced transposon is induced to move to new locations throughout the genome. In each case the newly inserted DNA may disrupt a gene function and this may be assayable phenotypically. In the context of this invention, the phenotype assayed would be lesion mimic phenotype, SAR gene expression, or UDS phenotype. The generation of T-DNA and transposon insertion mutant collections is a well documented technique in the literature and is well within the ordinary skill of the routineer (e.g. Feldman et al. (1989) *Science* 243: 1351–1354; Marks and Feldman (1989) *Plant Cell* 1: 1053–1050; Honma et al. (1993) *Proc. Natl. Acad. Sci. USA* 90: 6242–6246; and Aarts et al. (1993) *Nature* 363: 715–717.

For genes that are tagged by T-DNA insertions, the wild-type uninterrupted gene can be cloned by firstly cloning the T-DNA tagged gene, and then using sequences in the host genome that flank the T-DNA sequence as probes in the cloning of the wild-type gene. These techniques have been described by Feldman et al. (*Science* 243: 1351–1354 (1989)), Marks and Feldman (*Plant Cell* 1: 1053–1050 (1989);) and Hayashi et al. (*Science* 258: 1350–1352). For genes that are tagged by transposons, the wild-type uninterrupted gene can be cloned using similar techniques and these have been described by Honma et al. (*Proc. Natl. Acad. Sci. USA* 90: 6242–6246 (1993)) and Aarts et al. (*Nature* 363: 715–717 (1993)).

An alternate approach to the cloning of genes tagged by insertion mutations is the use of subtraction techniques in which genomic DNA or cDNA derived from lines that are isogenic for all but the mutation are repeatedly hybridized to remove homologous sequences. This causes an enrichment for the sequences that differ between the two populations and that are subsequently subcloned and characterized. This technique and numerous variations thereof have been described extensively in the literature viz. Lamar and Palmer (1984) *Cell* 37: 171–177; Kunkel et al. (1985) *Proc. Natl. Acad. Sci. USA* 82: 4778–4782; Nussbaum et al. (1987) *Proc. Natl. Acad. Sci. USA* 84: 6521–6525; Lisitsyn et al. (1993) *Science* 259: 946–951.

Having cloned the wild-type gene from which the mutant phenotype derives, the cDNA corresponding to this wild type gene can be easily isolated using hybridization techniques that are well known in the art. Once isolated, the cDNA can be expressed in transgenic plant lines in sense orientation (to achieve overexpression of the gene) or in antisense orientation (to turn off the endogenous gene).

Expression in transgenic plants is achieved by the fusion of the cDNA identified and cloned as described above behind a suitable promoter in sense or antisense orientation. The cDNA is cloned into a plant expression cassette behind a promoter expressed at high levels in transgenic plants and upstream of a transcriptional terminator that is known to function in plants. A preferred promoter is the CaMV 35S promoter and a preferred terminator is the nopaline synthase terminator. The expression cassette is transferred to a binary vector (pCGN1540—Alexander et al., *PNAS* 90: 7327–7331 (1993) for Agrobacterium transformation and a direct gene transfer vector (pCIB3064—Koziel et al., *Biotechnology* 11: 194–200) for direct gene transfer. Agrobacterium is particularly suitable for the transformation of dicotyledonous species and direct gene transfer is particularly suitable for the transformation of monocotyledonous species. Recently, tranformation of monocotyledons using Agrobacterium has also been described (WO 94/00977 and U.S. Pat. No. 5,591,616). These techniques are well known in the art and are described in the two above-cited publications. Transgenic plants are screened for expression of sense or antisense RNA by Northern analysis and plants that express at high levels are selected for further phenotypic analysis.

Alternatively, promoters can be selected that have tissue specific expression pattern and would thus localize the effects of sense or antisense expression to particular cell types (for examples of such promoters see Edwards and Coruzzi, *Ann. Rev. Genet.* 24: 275–303 (1990)). Additionally promoters can be selected that are chemically regulatable and can thus be induced to express the transgene upon treatment of the transgenic plant with a specific chemical. A suitable promoter for this is the PR-1a promoter from tobacco (U.S. Pat. No. 5,614,395).

The expression of the lsd, cim, and nim genes in transgenic plants in the appropriate host genotype background can be used to manipulate both disease resistance and/or host cell death. A transgene in sense or antisense, which may cause the host cell death phenotype (akin to the cell death apparent in the lesions of the lesion mimic mutants), can be expressed under the control of plant regulatory elements that are well known in the art to be expressed only in certain cell types (e.g. pollen or tapetal cells for the production of male sterility), or alternatively under the regulation of a chemically induced promoter (e.g. the PR-1a promoter). In one embodiment of the invention the transgene causing cell death (e.g. the cim1-derived gene in antisense) is expressed under a pollen specific promoter to cause male sterility in the female parent, whereas the pollinator carries a construct in antisense to the pollen specific construct (i.e. antisense-to-antisense), which is fused to the chemically regulatable PR-1a promoter. Thus, in the F1 hybrid plant population, treatment with the chemical inducer of the PR-1a promoter will activate the pollinator-line derived gene and block the expression of the mother parent-derived gene allowing normal flowering of the F1 hybrid. In an analogous fashion, lines can be created that are female sterile (by utilizing a promoter that is expressed in gynaecium tissue only). From the biology of lsd, cim, and nim mutants described in this specification, it is apparent that disease resistance phenotypes can be modified from the expression of antisense to lsd, cim, and nim genes. In the case of cim genes, elevated disease resistance would be expected, whereas for nim genes a reduction in disease resistance would be expected.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

The following examples are offered by way of illustration and not by way of limitation.

EXPERIMENTAL

I. Lesion Mimic Mutants

The class of mutants described in this section of examples corresponds to the "cim Class I" mutants described supra, are also referred to herein as lsd mutants.

Example 1

Arabidopsis Lesion Mimic Mutants

Lesion mimic mutants were isolated during a screen for Arabidopsis mutants with altered expression of a set of genes associated with systemic acquired resistance (SAR genes), such as PR-1, PR-2, and PR-5 (Ward et al. (1991)). EMS mutagenesis was conducted as follows: *Arabidopsis thaliana* ecotype Columbia seed was placed in a solution of EMS for 12–24 hours, the seed was then washed and planted. When the plants were mature, groups of 1000 plants were harvested and the seed was kept in a separately numbered lot. EMS-treated seed can also be purchased from Lehle seed, Tucson, Ariz. M2 EMS-treated seed was planted and plants were grown in individually marked containers. When the plants were three weeks old, one to two leaves were harvested from each plant. RNA was isolated from the leaf samples and analyzed using RNA gel blots probed with PR-1 and PR-2 cDNAs. Seed was isolated from plants that showed high level expression of these two RNAs. In addition, any interesting morphological phenotypes were noted.

One plant showed lesion-like symptoms on the leaf margins that expanded inward to the midrib of the oldest leaves. These lesions were first observable when the plant was approximately three weeks old when grown under 9 hour days. The gene conferring the trait that was mutated to give the phenotype was designated cim1 (aka lsd2). When progeny from this original plant were grown, approximately half had the lesion-mimic phenotype and high level SAR gene expression. The remainder of the plants looked phenotypically normal and had low-background levels of SAR gene expression. These results are consistent with the mutant cim1 gene having a dominant effect causing both the lesion mimic phenotype and altered gene expression and the original cim1 plant being heterozygous.

Example 2

Disease Resistance of the cim1 Mutant

The cim1 mutant was tested for susceptibility/resistance to infection by Pseudomonas and Peronospora. For the bacterial pathogen Pseudomonas, in planta bacterial growth was monitored over a five day period after inoculation by injection of $10^5$ colony forming units per ml using the procedure described by Debener et al. (1991) *Plant J*. 1: 289–302. Typically the cim1 mutant line resulted in a reduction in growth by an order of magnitude compared to wild-type. This indicated that the cim1 line had enhanced resistance to infection by Pseudomonas. To assess susceptibility/resistance of cim1 to the fungal pathogen *Peronospora parasitica*, 4 week old plants were either leaf inoculated using 2 ml of a suspension of fresh conidiospores in water (@$10^5$ spores/ml) or sprayed over the entire aerial plant surface (@$10^6$ spores/ml). The spore suspension was prepared as described by Dangl et al. (1993) *Int. Rev. Cytol.* 144: 53–83.

On comparison to wild-type, cim1 plants showed much less hyphal growth and conidiospore production. The leaf surfaces were visibly clearer of Peronospora mycelium than wild-type plants and the plants thus showed elevated resistance to the fungus. The table below shows a summary of data. The altered fungal morphology and resistance phenotype was similar to that shown in Arabidopsis plants pretreated with the SAR-inducing chemical INA (Uknes et al. (1992) *Plant Cell* 4: 645–656).

Peronospora parasitica Disease Ratings:

| Plant Line | Number of Plants Expressing Disease Levels[a] | | | | | | total # of plants |
|---|---|---|---|---|---|---|---|
| | 0 | + | ++ | +++ | ++++ | +++++ | |
| Wildtype | 0 | 0 | 0 | 0 | 0 | 20 | 20 |
| cim 1 | 0 | 6 | 7 | 0 | 0 | 0 | 13 |

This scale is defined as:
0: No conidiophores on plant;
+: At least 1 leaf with 1–5 conidiophores;
++: At least one leaf with 5–20 conidiophores;
+++: Many leaves with 5–20 conidiophores;
++++: All inoculated leaves with >5 conidiophores;
+++++: All inoculated leaves with >20 conidiophdres.

Example 3

Tobacco Lesion Mimic Mutants

Transgenic tobacco line 1791C-18-2, which was transformed with the SAR gene PR-Q, showed a lesion mimic phenotype. Fully expanded leaves had many 11–20 millimeter necrotic lesions. These lesions were typically light-brown at the center and surrounded by darkened tissue. When the plants were approximately 5 weeks old, they were infected with *Phytophthora parasitica* by soil application and resistance to *Phytophthora parasitica* was observed. However, other plants lines transgenic for PR-Q but not having the lesion mimic phenotype were not resistant to *Phytophthora parasitica*. This indicated that the observed resistance is caused by the altered phenotype of the plant (lesion mimic) and not the presence of the transgene.

Example 4

Construction and Characterization of the Transgenic Line 1791C-18-2, Constitutively Expressing PR-Q For general methods of preparing PR-Q, see U.S. Pat. No. 5,650,505, incorporated herein by reference.

A. Preparation of Purified PR-Q

Plants of *Nicotiana tabacum* cv. Xanthi.nc were grown in a greenhouse and infected when 8 weeks old by rubbing the leaves with a suspension of the common strain (U1) of tobacco mosaic virus at a concentration of 0.5 micrograms/ml, in a solution of 10 mM sodium phosphate (pH 7.0) containing carborundum. Leaves were harvested 7 days later. The intercellular-fluid fraction was made from the leaves by the vacuum infiltration method of Parent and Asselin, (1984) *Can. J. Bot.* 62:564–569. The proteins PR-P and PR-Q were separated from the other proteins present in the fraction by sequential purification through an Ultragel AcA54 column, a DEAE-Sephacel column, and a reverse-phase HPLC phenyl column, and their recovery was monitored by comparing samples of crude intercellular-fluid with the purified fraction on 10% nondenaturing gels as described by Gianninazzi and Kassanis (1974) *J. Gen. Vir.* 23:1–9. Pure PR-Q was obtained from the mixture of PR-Q and PR-P by chromatography on a Brownlee Labs AX-300 HPLC ion-exchange column, using a gradient of 10–250 mM ammonium acetate (pH 7.0).

B. Amino Acid Sequence of PR-Q

Cyanogen bromide and tryptic peptides were made and purified by methods well known in the art, and subjected to automated Edman degradation and analysis.

C. Isolation and Cloning of PR-Q cDNA

Tobacco leaves were infected as described and harvested 5 days later. RNA was prepared by the method of Lagrimini et al. (1987) *PNAS* 84:7542–7546, cDNA was made from it by the method of Gubler and Hoffman, (1983) *Gene* 25: 263–269, and the cDNA was cloned into the EcoRI site of the lambdaOngC phage vector available from Stratagene. The library was plated and duplicate filter replicas made. The filters were probed with DNA encoding the tobacco basic chitinase Shinshi et al. (1987) *PNAS* 84:89–93 under the following conditions: 125 MM NaCl/1% SDS/40 mM sodium phosphate, pH 7.2/1 mM EDTA at 50° C.; washing was done under the same conditions. Positive plaques were identified and isolated. The isolated phage were plated again, and new duplicate sets of filters made. The tobacco basic chitinase was again used as a probe, but this time the hybridization and washing were done in the previously described solution at 65° C. Plaques which hybridized to the probe at 50° C., but either did not or hybridized weakly at 65° C. were purified. DNA was isolated from the purified phage, and the cDNA removed by digesting with EcoRI. The EcoRI fragment representing the cDNA was subcloned into the plasmid vector Bluescript, and its sequence determined by dideoxy sequencing using the procedure for double-stranded templates. The identification of the clones as PR-Q was accomplished by comparing the predicted amino acid sequence derived from the cDNA with the amino acid sequence determined from the purified protein. The cDNA sequence of PR-Q is shown as SEQ ID NO:7 of U.S. Pat. No. 5,650,505.

D. Engineering PR-Q DNA Into Plant Expression/Transformation Vectors

The full-length PR-Q cDNA was inserted into the EcoRI site of the plasmid pCGN1761, which placed it between a duplicated 35S RNA promoter derived from the cauliflower mosaic virus and transcription termination signals encoded by the 3' noncoding region of the tml gene of the same virus. Recombinant plasmids were analyzed by restriction digest, and one that contained the PR-Q cDNA in the orientation appropriate for the production of a translatable PR-Q-encoding message, pCIB1022, was chosen for further constructions.

A DNA fragment containing the double CaMV promoter, PR-Q cDNA, and tml 3' region was excised from pCIB1022 by digesting it with XbaI. It was inserted into the XbaI site of the plasmid pCGN1540. The binary transfer vector pCGN1540 contains a gentamycin resistance gene for selection in both *E. coli* and *Agrobacterium tumefaciens*, and pBR322 and PRiHRI origins of replication. Insertion into the XbaI site places the PR-Q expression cassette between DNA sequences corresponding to the right and left borders of the Agrobacterium T-DNA, along with a cassette for expression of the Tn5 neomycin phosphotransferase gene under the control of the mannopine synthase promoter and bounded by the 3' non-coding region of the mannopine synthase gene, and an *E. coli* lacZ gene for color production. The structure of the new plasmid, pCGN17991C, was shown by restriction analysis to be the one in which the mas promoter and the double CaMV promoter would initiate transcription in the same direction on the DNA template.

E. Transformation of Tobacco

Plasmid pCGN1791C was transformed into *A. tumefaciens* strain LBA4404. Transformation of *Nicotiana tabacum* cv. Xanthi.nc was by co-cultivation of the bacteria with leaf disks by standard methods. Transformed plant tissue was selected by resistance to kanamycin, and was regenerated to intact plants (T1 plants) by standard methods. About twenty plants were regenerated, starting with tissue that arose from independent transformation events.

F. Production and Biochemical Characterization of Homozygous Plants

Small samples of leaf tissue were taken from each of the T1 plants and denatured extracts from total leaf tissue were analyzed by SDS gels and Western blots, using antisera raised against PR-Q protein. The material from the transgenic plants that reacted with the antibody was compared to that which came from TMV-treated, untransformed tobacco, to material from untreated, untransformed tobacco, and to purified PR-Q protein on the same blot. Transgenic plants that did not contain a significant amount of immunoreactive material that was the correct molecular weight were discarded. The plants that were positive in this test were grown in a greenhouse until the flowering stage, and then they were individually bagged to ensure that only self-fertilization took place. The resulting seeds (T2 generation) were harvested, and 100 seeds from each T1 plant were scored for resistance to kanamycin by germinating them on antibiotic-containing medium. Plants that gave seeds exhibiting approximately a 3:1 ratio of kanamycin resistance to sensitivity were judged to contain a single locus of T-DNA insertion. 8–10 offspring from each of these plants were grown to the flowering stage and bagged. During the growth of these plants, leaf samples were taken and analyzed for constitutive PR-Q expression as described. Based on these analyses, a lineage from one independent transformant was chosen as the one that accumulated the largest amount of PR-Q (1791C-18). Seeds from the individual T2 plants of this lineage were harvested and 100 were scored for kanamycin resistance. The complete absence of kanamycin sensitive seeds in this assay indicated that the seeds were derived from a parent homozygous for the transgene. Seed lot 179 1C-18-2 was homozygous by this criterion, and was used for testing against pathogens.

Example 5
Test For Resistance To *Cercospora nicotianae*

Inoculum from *C. nicotianae* (ATCC strain 18366) was made by culturing a conidial suspension on CDV8 plates covered with sterile filter paper under black lights at 18° C. for two weeks. The spores were collected by brushing the filter paper in distilled water, and the spore concentration was adjusted to 100,000–150,000 spores per ml. The suspension was sprayed onto the upper surface of the leaves of 8-week-old tobacco plants, which were then kept covered for 5–6 days by a plastic sheet to maintain high humidity. After that, the plants were kept moist by periodic spraying by an automatic system. The symptoms appeared 8–10 days later, and disease scores were obtained by recording the percent of leaf area infected by the fungus. The lesion mimic plants, 1791C-18-2, were significantly less infected than untransformed Xanthi.nc plants.

II. Phenotypically Normal Constitutive Immunity (cim) Mutants

The class of mutants described in this section of examples corresponds to the "cim Class II" mutants described supra, which are also referred to herein as cim mutants.

Example 6
Isolation and Characterization of Phenotyically Normal cim Mutants With Constitutive SAR Gene Expression 1100 individual M2 mutagenized (EMS) Arabidopsis plants were grown in Aracon trays (Lehle Seeds, Round Rock, Tex.) in sets of approximately 100. Plants were grown as described in Uknes et al. (1993) with special attention given to avoid over-watering and pathogen infection. Briefly, Metro Mix 360 was saturated with water and autoclaved three times for 70 minutes in 10-liter batches. The potting mix was stirred thoroughly in between each autoclaving. Seeds were surface sterilized in 20% Clorox for 5 minutes and washed with seven changes of sterile water before sowing. Planted seeds were vernalized for 3–4 days followed by growth in chambers with a 9 hour day and 15 hour night at 22° C. When the plants were three to four weeks old, one or two leaves, weighing 50 to 100 mg, were harvested and total RNA was isolated using a rapid, mini-RNA preparation (Verwoerd et al. (1989) *Nuc. Acid Res.* 17, 2362). PR-1 gene expression was analyzed by Northern blot analysis (Lagrimini et al. (1987) *Proc. Natl. Acad. Sci.* USA 84, 7542–7546; Ward et al. (1991)). Each set of plants also contained a non-treated *A. thaliana* Col-0 and a 2-day INA-treated (0.25 mg/ml) control. All plants were maintained as described in Weymann et al., (1995).

80 putative mutants accumulating elevated levels of PR-1 mRNA were identified. Following progeny testing, five were chosen for further characterization. Putative cim mutants displayed elevated SAR gene expression in the absence of pathogen or inducing treatment. Progeny testing of the putative cim mutants confirmed that constitutive PR-1 expression was heritable. Of the cim mutants, two, cim2 and cim3, with the highest, most stable expression of PR-1 were characterized further.

Back crosses to Columbia utilized the recessive glabrous trait as a marker for identification of F1 progeny. Col-gl1 flower buds were emasculated prior to pollen shed, and pollen from the mutants was applied immediately and the following day. F1 plants were grown in soil and the out crossed plants were identified by the presence of trichomes.

Following crosses of cim2 and cim3 to ecotype Col-0 or La-er, a large proportion of F1 plants were identified with high SAR gene expression, suggesting these traits were dominant. In the case of cim2, some, but not all, F1 plants had constitutive SAR gene expression. Such a result would be expected if the cim2 mutant were dominant and carried as a heterozygote in the parent. Further genetic testing of cim2 showed continued variable segregation in the F2 generation, consistent with incomplete penetrance.

The heterozygous cim3 demonstrated a 1:1 segregation in the F1 generation whereupon two individual F1 plants expressing a high level of PR-1 mRNA were selfed to form an F2 population. F2 segregation, obtained by scoring PR-1 mRNA accumulation, showed 93 F2 plants with high PR-1 mRNA and 25 F2 plants without significant PR-1 mRNA accumulation giving a 3.7:1 ratio ($C^2=1.77$; $0.5>P>0.1$), which is consistent with the hypothesis that cim3 is a dominant, single gene mutation. Subsequent outcrosses confirmed that cim3 was inherited as a dominant mutation.

For cim3, the original M2 plant identified in the screen and the M3 population appeared normal. However, as the cim3 plants were selfed, some of the best expressing lines had low fertility. Following the back cross to Col-gl1, plants with normal appearance and fertility and strong PR-1 expression were obtained.

When initially identified, cim3 also appeared slightly dwarfed with thin, distorted leaves. However, F2 plants resulting from a cross with ecotype Col-gl1 retained high SAR gene expression and could not be distinguished from wild-type plants. This suggested that the dwarfed, distorted-leaf phenotype was caused by an independent mutation that was not associated with constitutive SAR gene expression. The cim3 mutant phenotype was also observed when plants were grown in sterile conditions confirming that PR-1 mRNA accumulation was not caused by a pathogen.

Example 7
SAR Gene Expression

In addition to PR-1, two other SAR genes, PR-2 and PR-5, were also highly expressed in cim3. Levels of SAR gene expression varied between the progeny, but were always more than 10-fold higher than the untreated control and similar to the levels obtained following a resistance-inducing INA (0.25 mg/ml) treatment of wild-type plants.

Example 8
Salicylic Acid Analysis

Endogenous concentrations of SA have been shown to increase following pathogen-induced necrosis in Arabidopsis (Uknes et al. (1993)). Salicylic acid and its glucose conjugate were analyzed as described in Uknes et al. (1993). Leaf tissue was harvested from 10 cim3 and 10 control, 4 week-old plants. Leaves from individual plants were harvested and analyzed for PR-1 gene expression. SA levels were measured from plants expressing PR-1. The concentration of free SA in cim3 was 3.4-fold higher than in non-infected wild-type Arabidopsis (233±35 vs. 69±8 ng/g fresh weight, respectively). The glucose conjugate of SA (SAG) was 13.1-fold higher in cim3 than in non-infected wild-type Arabidopsis (4519±473 vs. 344±58 ng/g fresh weight, respectively). These increased levels of SA and SAG are comparable to the levels that have been reported for either pathogen-infected tissue or the cpr mutant (Bowling et al., *Plant Cell* 6, 1845–1857 (1994)).

Example 9
Disease Resistance cim3 was evaluated for resistance to *Peronospora parasitica* (NoCo2), the causal agent of downy mildew disease of Arabidopsis. Thirty cim3 (confirrned by PR-1 RNA expression) and thirty control plants (ecotype Columbia), each about 4 weeks old, were inoculated with *P. parasitica*, as described in Uknes, et al. (1992). Seven days later, plants were analyzed for sporulation and stained with trypan blue to visualize fungal structures, as described in Keogh et al. (1980) *Trans. Br. Mycol. Soc.* 74, 329–333; and in Koch and Slusarenko (1990) *Plant Cell* 2, 437–445. Wild-type (Col-0) plants support the growth of hyphae, conidia, and oospores, while wild type plants treated with INA (0.25 mg/ml) and cim3 plants showed no fungal growth. The cim3-mediated resistance is typically seen as a small group of dead cells at the site of pathogen infection. This type of resistance is similar to that seen in lsd mutants (Dietrich et al. (1994); Weymann et al., (1995)), or in wild-type plants in which SAR has been induced (Uknes et al. (1992)). Occasionally, intermediate resistance phenotypes were observed, including trailing necrosis in the wake of the hyphal tip in cim3 plants. This trailing necrosis is similar to that found in wild-type plants treated with low doses of SA or INA (Uknes et al. (1992); Uknes et al. (1993)). However, sporulation was never observed on cim3 plants while all control plants showed sporulation. No spontaneous lesions were observed on uninoculated cim3 leaves when stained with trypan blue.

In addition to resistance to the fungal pathogen *P. parasitica*, cim3 was also resistant to infection with the bacterial pathogen *Pseudomonas syringae* DC3000. Six-week-old wild-type (±INA treatment) and cim3 plants were inoculated with a suspension of *P. syringae* DC3000 and the progress of the disease was followed by monitoring the growth of the bacteria extracted from infected leaves over time. The difference in bacterial titers between Col-O, Col-O+INA, and cim3 at either day 0 or day 2 was not statistically significant. However, by day four, there was a 31-fold decrease in bacterial growth between wild-type and cim3 plants (P<0.003; Sokal and Rohlf, 1981). The plants were also visually inspected for disease symptoms. Leaves from wild-type plants were severely chlorotic with disease symptoms spreading well beyond the initial zone of injection. In contrast, either wild-type plants pretreated with INA or cim3 plants were nearly devoid of disease symptoms.

For the experiments described herein, cultures of *Pseudomonas syringae* pv. tomato strain DC3000 were grown on King's B media (agar plates or liquid) plus rifampicin (50 µg/ml) at 28° C. (Walen et al. (1991) *Plant Cell* 3, 49–59). An overnight culture was diluted and resuspended in 10 mM $MgCl_2$ to a density of $2–5 \times 10^5$ cells per ml and injected into Arabidopsis leaves. Injections were carried out by creating a small hole with a 28 gauge needle midway up the leaf and then injecting approximately 250 µl of the diluted bacterial solution with a 1 cc syringe. At various time points, 10 random samples consisting of 3 random leaf punches from a #1 cork borer were taken from 10 plants from each treatment. The 3 leaf punches were placed in an eppendorf tube with 300 µl of 10 mM $MgCl_2$ and ground with a pestle. The resulting bacterial suspension was appropriately diluted and plated on King's B media plus rifampicin (50 µg/ml) and grown for 4 days at 28° C. Bacterial colonies were counted and the data were subjected to Student's t statistical analysis (Sokal and Rohlf (1981), Biometry, $2^{nd}$ ed. New York: W. H. Freeman and Company).

Also for the experiments described herein, 2,6-dichloroisonicotinic acid (INA) was suspended in sterile, distilled water as a 25% active ingredient formulated in a wettable powder (0.25 mg/ml, 325 µM; Kessmann et al. (1994) *Annu. Rev. Phytopathol* 32, 439–59). All plants were sprayed with water or INA solutions to the point of imminent runoff.

Example 10
The Role of SA in SAR Gene Expression and Disease Resistance

To investigate the relationship between SA, SAR gene expression, and resistance in cim3, crosses were carried out with Arabidopsis plants expressing the salicylate hydroxylase (nahG) gene (Delaney et al. (1994)). These "NahG plants" were made by transformation of the 35S driven nahG gene into Arabidopsis using Agrobacterium-mediated transformation. See, Huang, H. Ma, H. (1992) *Plant Mol Biol Rep.* 10, 372–383, herein incorporated by reference; Gaffney, et al. (1993) *Science* 261, 754–756, herein incorporated by reference; and Delaney, et al. (1994) *Science* 266, 1247–1250, herein incorporated by reference. Col-nahG Arabidopsis carries a dominant kanamycin resistance gene in addition to the dominant nahG gene, so Col-nahG was used as the pollen donor. F1 seed was hydrated in water for 30 minutes and then surface sterilized in 10% Clorox, 0.05% Tween 20 for five minutes, and washed thoroughly in sterile water. Seeds were plated onto germination media (GM, Murashige and Skoog medium containing 10 g/L sucrose buffered with 0.5 g/L 2-(N-morpholino) ethanesulfonic acid, pH 5.7 with KOH) containing 25 mg/ml kanamycin to select for $F_1$ plants. See, Valvekens et al. (1988) *Proc. Natl. Acad. Sci.*, USA 85, 5536–5540. Kanamycin-resistant $F_1$ plants were transferred to soil after 18 days. The presence of the nahG gene and PR-1 expression was confirmed in all experiments by Northern blot analysis.

Because both the cim3 mutant and nahG phenotypes are dominant, epistasis between the two genes could be analyzed in F1 plants. Seventy F1 plants from a cim3 X nahG cross were analyzed for PR-1 and nahG gene expression. In Northern blot analysis of mRNA expression, the presence of the nahG gene correlated with suppressed SAR gene expression. The presence of cim3 in each F1 was confirmed by assessing PR-1 mRNA in the resulting F2 segregants.

To determine if the cim3 mutation was epistatic to nahG with respect to disease resistance, 5 F1 plants from the cim3 X nahG cross, which had been confirmed for the presence of nahG and absence of PR-1 mRNA, were selfed, and 20–30 F2 seed were planted. Expression of nahG and PR-1 mRNA was analyzed in individuals from this F2 population, which were then challenged with *P. parasitica* (NoCo2) to assess their disease susceptibility. Disease resistance conferred by cim3 was eliminated by the presence of the nahG gene, demonstrating that nahG is epistatic to cim3 for SAR gene expression and the disease resistance phenotype.

Example 11
Construction of a Transgenic Plant Line Harboring a Chimeric PR-1 Promoter/Luciferase (PR-1/luc) Construct A. Construction of the PR-1/Luciferase Chimeric Gene A PR-1 genomic clone was identified by screening an Arabidopsis EMBL 3 genomic library (Clontech) with the PR-1 cDNA (Uknes et al. (1992)). A 7kb XhoI fragment of the PR-1 genomic clone was subcloned into pBS+ (Stratagene) using standard cloning techniques (Sambrook et al. (1989)). Restriction mapping revealed the presence of a 4.2 kb promoter fragment 5' of the PR-1 coding region (U.S. Pat. No. 5,614,395). This fragment was sequenced and subcloned 5' to a cDNA coding for firefly luciferase (excised from pDO432; Ow et al. (1986) *Science*, 235: 856–859) generating a translational fusion at the ATG that marks the start of translation for luciferase. No terminator sequence was added because the firefly luciferase gene contains an consensus polyadenylation signal (AATAAA) 3' of the stop codon of luciferase that is recognized as terminator of transcription in plants. The PR-1/luciferase construct was verified by sequencing and subcloned as a XboI/SacI fragment into pCIB200, a binary vector that contains the neomycinphosphotransferase II gene that confers resistance to kanamycin. The resulting construct was transformed into *Agrobacterium tumefaciens* strain GV3101 by electroporation (Holsters et al. (1978) *Molec. Gen. Genet.* 163, 181–187). The DNA sequence of the chimeric PR-1/luc construct is presented as SEQ ID NO:1.

B. Transgenic Plants

Arabidopsis plants were transformed with either PR-1/luciferase (ecotypes Col-O and Dijon) or 35S/nahG (ecotype Dijon) by Agrobacterium using the vacuum-infiltration method (Bechtold et al. (1993) *Comptes Rendus de l'Academie des Sciences* (Paris) 316, 1194–1199) or by root transformation. For each line, at least 32 independent transformants homozygous for the transgene were identified based on resistance of the T3 progeny to kanamycin (PR-1/luciferase) or hygromycin (35S/nahG). Col-O was chosen as a suitable background for genetic analysis and Dijon has the advantage that inoculation with the viral pathogen turnip crinkle virus (TCV) triggers a hypersensitive response (Uknes et al. (1993) MPMI 6, 692–698).

Example 12
Induction of Luciferase Activity in Transgenic Plants

A. Chemical Induction

PR-1/luc plants were characterized based on inducibility of luciferase activity by 375 µM INA. Lines that consistently showed more than 1000-fold inducibility (6E in Col-O and B1 in Dijon) were selected for further experimentation. A 35S/nahG line in the Dijon ecotype was selected as described in Lawton et al. (1995).

For determination of chemical inducibility of luciferase activity, 6E plants were sprayed with three known chemical activators of SAR: SA (5 mM), INA (375 µM), or BTH (375 µM and 5 mM). In vitro luciferase activity was determined every 24 hours during a period of four days. For each measurement, six samples consisting of six leaves each were harvested. INA and BTH treatment at the standard concentration of 375 µM caused an induction of luciferase of more than 2000 fold within 48 hours; this level was maintained for at least two more days. In contrast, treatment with 5 mM SA led to a 5000 fold induction of luciferase activity within 24 hours, which was followed by a decline that was possibly due to inactivation of SA. Treatment with 5 mM BTH caused an induction similar to SA, but no pronounced decline of activity was observed within the first four days.

RNA was extracted from the same tissue samples used for luciferase determination, and PR-1 mRNA levels were visualized by Northern blotting. Induction of PR-1 mRNA and luciferase correlated quantitatively, indicating that luciferase activity reflects PR-1 transcription in these plants. To test whether the onset of SAR gene expression could be monitored in vivo, PR-1/luc plants were treated with 0.375 µM BTH and sprayed with luciferin 2 days after treatment. Light emission was followed using a sensitive photon-imaging system (Argus 50 software, video camera model XC77, Hamamatsu Inc., Bridgewater, N.J., USA). Light emission of seedlings grown in vitro could be detected within 2 minutes.

B. Biological Induction

To determine biological inducibility of luciferase activity, both the B1 and a B1-nahG line were inoculated with TCV, and luciferase activity was measured over a time course of 9 days. For each measurement, six samples consisting of six leaves each were harvested from both inoculated leaves and secondary non-inoculated leaves of treated B1 and B1-nahG plants. Infected leaves of B1 plants displayed a linear increase in luciferase activity following a 1 day lag period similar to the accumulation of PR-1 mRNA in the same tissue. The same treatment of B1-nahG plants led to a comparably small increase of luciferase after 9 days. In the systemic leaves of TCV-treated plants, a clear induction of both luciferase activity and PR-1 mRNA was observed by 5 days. This induction was found only in the B1, not in the B1-nahG line, supporting the theory that SA is required for signal transduction in SAR (Gaffney et al. (1993)).

Taken as a whole, the above data demonstrates that induction of SAR gene expression can be monitored by following luciferase activity in PR-1/luc plants.

Example 13

In vivo Monitoring of SAR Gene Expression

To determine whether the onset of SAR gene expression could be monitored in vivo, PR-1/luc plants (Dijon) were inoculated with TCV. Nine days after treatment, the plants were sprayed with luciferin. Light emission of systemic non-infected leaves of TCV-treated plants was detected within two minutes, whereas leaves of mock inoculated plants could not be recognized following integration of photon emission over a one hour period. The three TCV-inoculated leaves emitted 10 to 50 times more photons than uninfected leaves. Chemical induction of SAR gene expression led to a more uniform distribution of light emission, indicating that the pattern observed after TCV treatment was not due to an artifact such as uneven distribution of luciferin but reflects a biological phenomenon in SAR.

Example 14

PR-1/luc Screen For cim Mutants

The PR-1/luc line (Col-O) was mutagenized by EMS (0.2% EMS, 12 hrs, 23° C., p-value=0.136, Lehle Seeds, Tucson, Ariz.). 168 pooled M1 populations were planted for M2 seeds. M2 populations were screened with more than 99% coverage of the M1 pool for constitutive expression of the PR-1/luciferase reporter gene. Four weeks old siblings were misted with a 7.5 mM luciferin solution and after a 10 min incubation, photon emission was integrated for 10 min in a photon imaging device (Hamamatsu Inc., Tokyo) equipped with an ARGUS 50 photon counting image processor at the most sensitive level.

Out of 250,000 plants screened, 605 plants showed high levels of luciferase activity in the screen. Luciferase activity in vivo was confirmed by a luciferase in vitro assay. One leaf was ground in 500 µl phosphate buffer (pH 7.8) at 4° C., 100 µl were mixed with 100 µl commercial luciferase substrate (Promega Corp., Madison, Wis.), and photon emission was counted for 10 sec in a luminometer Monolight 2010 (Analytical Luminescence Laboratory, Ann Arbor, Mich.). 249 of the 605 mutants were lethal or sterile; the remaining 356 were retested for luciferase activity in the next generation.

266 mutants displayed visible lesion formation, whereas 90 mutants did not display obvious spontaneous cell death. The 90 mutants (derived from 82 different M2 groups) were analyzed for PR-1 mRNA levels by Northern blotting, resistance to the virulent pathogen Peronospora parasitica pv Noco2 (scored 8 days after inoculation with $10^5$ spores/ml), salicylic acid levels, and lesion formation by staining with the viable stain lactophenol trypan blue. All 90 mutants displayed both elevated luciferase activity and elevated levels of PR-1 mRNA. Interestingly, no mutant was identified where luciferase and PR-1 expression was uncoupled.

To clearly distinguish between cim's and lsd's, leaves of all 90 mutants were subjected to trypan blue staining, which reveals areas of spontaneous cell death (Dietrich et al. (1994)). Even though the 90 mutants were preselected against obvious lesion formation, 74 mutants were found to belong to the lsd class (cim class I). 16 mutants (derived from 16 different M2 groups) were assigned to the cim class (cim class II or III), as no spontaneous cell death was detectable under several growth conditions (long day or short day; high light or low light intensity). These data demonstrate that careful analysis is required before a mutant is claimed to show constitutive immunity in the absence of spontaneous lesion formation.

SAR gene expression, resistance to P. parasitica NoCo2, and SA levels were examined to further investigate if this set of 90 mutants was affected in SAR signal transduction. SAR gene expression was determined by examination of the three marker genes PR-1, PR-2, and PR-5 (Uknes et al. (1992)) in mutants belonging to the cim class and the lsd class. Both cim and lsd mutants display elevated levels of not only PR-1, but also PR-2 and PR-5 mRNA similar to levels reached in a BTH treated plant, which suggests that increased luciferase activity reflects coordinated induction of SAR genes. All cim's and all lsd's were found to show increased resistance to P. parasitica consistent with a phenotype of constitutive SAR. All of the cim's and lsd's investigated also displayed elevated levels of salicylic acid, suggesting that these mutations cause elevated levels of SA, which subsequently triggers activation of SAR.

cim mutants were also crossed to NahG plants as described earlier, which resulted in decreased SA accumulation as expected. Interestingly, one cim mutant isolated through the PR-1/luc screen remained resistant to P. parasitica even with the decreased SA accumulation resulting from the cross to the NahG plant line. Such disease resistance exhibition despite decreased SA accumulation suggests that this particular cim mutant may belong to cim class III.

Example 15
Disease Resistance Against *Erysiphe cichoracearum* cim's were evaluated for resistance to *Erisyphe cichoracearum*, the causal agent of powdery mildew disease of Arabidopsis. Four-week old, confirmed cim mutant plants, Col-0 plants, confirmed cim-mutant plants treated with 0.3 mM BTH (two days before inoculation), and Col-0 plants treated with 0.3 mM BTH (two days before inoculation) were inoculated to high density with *Erysiphe cichoracearum*, as described in Adam and Somerville (1996) *Plant Journal* 9 (3), 341–356. Ten days later, disease progression was quantified by counting infected leaves: 0–1 infected leaf per plant=rating 1; 2–4 infected leaves=rating 2; ≧5 leaves infected=rating 3. In addition, fungal hyphal growth was visualized by a fluorescent dye staining, 3,3'-dihexyloxacarbocyanine iodide (Duckett and Read (1991) *New Phytol*. 118, 259–272), as described in Shunyuan et al. (1997) *Plant Journal* 12(4), 757–768. Col-0 plants supported the growth of *Erysiphe cichoracearum* (rating 2.9 or above), while all BTH-treated plants exhibited complete resistance (rating 1.0). Several cim mutants mimicked this resistance (rating 1.1–1.5).

III. Non-inducible Immunity (nim) Mutants

The class of mutants described in this section do not express SAR genes, even when induced by a pathogen. Consequently, these mutants have a universal disease susceptible (UDS) phenotype.

Example 16
Use of nim Mutants in Disease Testing nim mutants are challenged with numerous pathogens and found to develop larger lesions more quickly than wild-type plants. This phenotype is referred to as UDS (i.e. universal disease susceptible) and is a result of the mutants failing to express SAR genes to effect the plant defense against pathogens. The UDS phenotype of nim mutants renders them useful as control plants for the evaluation of disease symptoms in experimental lines in field pathogenesis tests where the natural resistance phenotype of so-called wild-type lines may vary (i.e. to different pathogens and different pathotypes of the same pathogen). Thus, in a field environment where natural infection by pathogens is being relied upon to assess the resistance of experimental lines, the incorporation into the experiment of nim mutant lines of the appropriate crop plant species would enable an assessment of the true level and spectrum of pathogen pressure, without the variation inherent in the use of non-experimental lines.

Example 17
Assessment of the Utility of Transgenes for the Purposes of Disease Resistance nim mutants are used as host plants for the transformation of transgenes to facilitate their assessment for use in disease resistance. A nim mutant line, characterized by its UDS phenotype, is used for subsequent transformations with candidate genes for disease resistance thus enabling an assessment of the contribution of an individual gene to resistance against the basal level of the UDS nim mutant plants. Preferably, an Arabidopsis nim mutant line is used; however, UDS phenotype plants of any species may be used as well.

Example 18
nim Mutants as a Tool in Understanding Plant-Pathogen Interactions nim mutants are useful for the understanding of plant pathogen interactions, and in particular for the understanding of the processes utilized by the pathogen for the invasion of plant cells. This is so because nim mutants do not mount a systemic response to pathogen attack, and the unabated development of the pathogen is an ideal scenario in which to study its biological interaction with the host.

Of further significance is the observation that a host nim mutant may be susceptible to pathogens not normally associated with that particular host, but instead associated with a different host. For example, Arabidopsis nim mutants are characterized by the UDS phenotype. These plants are challenged with a number of pathogens that normally only infect tobacco, and found to be susceptible. Thus, the nim mutation causing the UDS phenotype leads to a modification of pathogen-range susceptibility and this has significant utility in the molecular, genetic and biochemical analysis of host-pathogen interaction.

Example 19
nim Mutants for Use in Fungicide Screening nim mutants are particularly useful in the screening of new chemical compounds for fungicide activity. nim mutants selected in a particular host have considerable utility for the screening of fungicides using that host and pathogens of the host. The advantage lies in the UDS phenotype of the mutant that circumvents the problems encountered by the host being differentially susceptible to different pathogens and pathotypes, or even resistant to some pathogens or pathotypes. By way of example nim mutants in wheat could be effectively used to screen for fungicides to a wide range of wheat pathogens and pathotypes as the mutants would not mount a resistance response to the introduced pathogen and would not display differential resistance to different pathotypes that might otherwise require the use of multiple wheat lines, each adequately susceptible to a particular test pathogen. Wheat pathogens of particular interest include (but are not limited to) *Erisyphe graminis* (the causative agent of powdery mildew), *Rhizoctonia solani* (the causative agent of sharp eyespot), *Pseudocercosporella herpotrichoides* (the causative agent of eyespot), *Puccinia* spp. (the causative agents of rusts), and *Septoria nodorum*. Similarly, nim mutants of corn would be highly susceptible to corn pathogens and therefore useful in the screening for fungicides with activity against corn diseases.

nim mutants have further utility for the screening of a wide range of pathogens and pathotypes in a heterologous host i.e. in a host that may not normally be within the host species range of a particular pathogen and that may be particularly easily to manipulate (such as Arabidopsis). By virtue of its UDS phenotype the heterologous host is susceptible to pathogens of other plant species, including economically important crop plant species. Thus, by way of example, the same Arabidopsis nim mutant could be infected with a wheat pathogen such as *Erisyphe graminis* (the causative agent of powdery mildew) or a corn pathogen such as *Helminthosporium maydis* and used to test the efficacy of fungicide candidates. Such an approach has considerable improvements in efficiency over currently used procedures of screening individual crop plant species and different cultivars of species with different pathogens and pathotypes that may be differentially virulent on the different crop plant cultivars. Furthermore, the use of Arabidopsis has advantages because of its small size and the possibility of thereby undertaking more tests with limited resources of space.

Although the foregoing invention has been described in some detail by way of illustration and example for purposes of clarity of understanding, it will be obvious that certain changes and modifications may be practiced within the scope of the appended claims.

What is claimed is:

1. A method for selecting, from a population of plants, one or more mutant plants that are susceptible to viral, bacterial, or fungal pathogens, said method comprising;
   a) evaluating the expression of SAR genes in plants that have a universal disease susceptibility (UDS) phenotype; and
   b) selecting one or more plants that fail to express SAR genes upon infection by viral, bacterial, or fungal pathogens or upon treatment with a chemical inducer of SAR, and therefore fail to effect a defense against viral, bacterial, or fungal pathogens.

2. The method of claim 1, wherein said plants are Arabidopsis.

3. A method for selecting, from a population of plants, one or more mutant plants that are incapable of expressing SAR genes, said method comprising:
   a) evaluating the expression of SAR genes in plants; and
   b) selecting one or more mutant plants that fail to express SAR genes upon infection by viral, bacterial, or fungal pathogens or upon treatment with a chemical inducer of SAR, and therefore have a universal disease susceptibility (UDS) phenotype.

4. The method of claim 3, wherein said plants are Arabidopsis.

5. A method for producing a mutant plant that is susceptible to viral, bacterial, or fungal pathogens, said method comprising propagating a mutant plant selected according to the method of claim 1.

6. A method for producing a mutant plant that is susceptible to viral, bacterial, or fungal pathogens, said method comprising propagating a mutant plant selected according to the method of claim 2.

7. A method for producing a mutant plant that is susceptible to viral, bacterial, or fungal pathogens, said method comprising propagating a mutant plant selected according to the method of claim 3.

8. A method for producing a mutant plant that is susceptible to viral, bacterial, or fungal pathogens, said method comprising propagating a mutant plant selected according to the method of claim 4.

9. A method for generating a line of mutant plants that are susceptible to viral, bacterial, or fungal pathogens, said method comprising propagating a mutant plant selected according to the method of claim 1.

10. A method for generating a line of mutant plants that are susceptible to viral, bacterial, or fungal pathogens, said method comprising propagating a mutant plant selected according to the method of claim 2.

11. A method for generating a line of mutant plants that are susceptible to viral, bacterial, or fungal pathogens, said method comprising propagating a mutant plant selected according to the method of claim 3.

12. A method for generating a line of mutant plants that are susceptible to viral, bacterial, or fungal pathogens, said method comprising propagating a mutant plant selected according to the method of claim 4.

* * * * *